(12) United States Patent
Dick et al.

(10) Patent No.: US 9,622,706 B2
(45) Date of Patent: Apr. 18, 2017

(54) CATHETER FOR IN VIVO IMAGING

(75) Inventors: Larry Dick, San Antonio, TX (US);
Thomas E. Milner, Austin, TX (US);
Daniel D. Sims, San Antonio, TX (US)

(73) Assignee: Volcano Corporation, San Diego, CA (US)

( * ) Notice: Subject to any disclaimer, the term of this patent is extended or adjusted under 35 U.S.C. 154(b) by 1270 days.

(21) Appl. No.: 12/172,922

(22) Filed: Jul. 14, 2008

(65) Prior Publication Data

US 2009/0018393 A1   Jan. 15, 2009

Related U.S. Application Data

(60) Provisional application No. 60/949,511, filed on Jul. 12, 2007.

(51) Int. Cl.
*A61B 1/04* (2006.01)
*A61B 5/00* (2006.01)
*A61B 1/00* (2006.01)
*A61B 8/12* (2006.01)
*A61B 8/00* (2006.01)

(52) U.S. Cl.
CPC .......... *A61B 5/6852* (2013.01); *A61B 5/0062* (2013.01); *A61B 5/0066* (2013.01); *A61B 8/12* (2013.01); *A61B 8/4461* (2013.01)

(58) Field of Classification Search
CPC .............. A61B 1/00163; A61B 1/0017; A61B 1/00183; A61B 5/0062; A61B 5/0066; A61B 5/6852; A61B 8/4461; A61M 25/0068

USPC ....... 600/114, 121, 129, 174, 139, 140, 144; 604/103.04
See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |

(Continued)

FOREIGN PATENT DOCUMENTS

EP   1041373 A2   10/2000
EP   01172637 A1   1/2002

(Continued)

OTHER PUBLICATIONS

U.S. Appl. No. 12/173,004, filed Jul. 14, 2008, Castella.

(Continued)

*Primary Examiner* — Timothy J Neal

(57) ABSTRACT

A catheter for in vivo imaging comprising a monolithic outer sheath terminating in a monolithic atraumatic tip having a guidewire lumen. The catheter for in vivo imaging comprising a rotary drive shaft that passes through a central lumen of the monolithic outer sheath to impart rotary motion.

12 Claims, 19 Drawing Sheets

(56) References Cited

U.S. PATENT DOCUMENTS

| | | |
|---|---|---|
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo ..................... 128/772 |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo ..................... 128/772 |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A * | 8/1995 | Ginn et al. ..................... 604/510 |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth ................ 204/298.21 |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |

(56) References Cited

U.S. PATENT DOCUMENTS

| | | |
|---|---|---|
| 5,916,194 A | 6/1999 | Jacobsen et al. |
| 5,921,931 A | 7/1999 | O'Donnell et al. |
| 5,925,055 A | 7/1999 | Adrian et al. |
| 5,932,035 A * | 8/1999 | Koger ................... A61B 8/12 148/563 |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. ....... 600/585 |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler .................. 600/467 |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. .................. 607/122 |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |

(56) References Cited

U.S. PATENT DOCUMENTS

| | | | |
|---|---|---|---|
| 6,730,107 B2 * | 5/2004 | Kelley et al. ............ 604/103.04 |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,029,436 B2 * | 4/2006 | Iizuka et al. ............ 600/160 |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |

(56) References Cited

U.S. PATENT DOCUMENTS

| | | |
|---|---|---|
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1* | 11/2001 | White et al. ............. 600/585 |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1* | 7/2002 | Crowley ............. 600/439 |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1* | 1/2003 | Izatt et al. ............. 600/425 |
| 2003/0013952 A1* | 1/2003 | Iizuka et al. ............. 600/407 |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. ............. 604/525 |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1* | 6/2004 | Moriyama ............. 600/140 |
| 2004/0111552 A1 | 6/2004 | Arimilli et al. |

(56) References Cited

U.S. PATENT DOCUMENTS

| | | |
|---|---|---|
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2004/0267196 A1* | 12/2004 | Miki et al. ............... 604/103.04 |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. ........ 600/139 |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. ................ 600/434 |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. ............... 600/433 |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. ............... 600/478 |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. .................... 600/459 |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne ....................... 600/585 |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke ..................... 623/1.11 |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. ............... 600/173 |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. ............... 600/115 |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |

(56) References Cited

U.S. PATENT DOCUMENTS

| | | |
|---|---|---|
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |

(56) References Cited

U.S. PATENT DOCUMENTS

| | | |
|---|---|---|
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | | | |
|---|---|---|---|---|
| EP | 2438877 A2 | 4/2012 | | |
| GB | 2280261 A | 1/1995 | | |
| JP | 11056786 A | 3/1999 | | |
| JP | 2000-262461 A | 9/2000 | | |
| JP | 2000-292260 A | 10/2000 | | |
| JP | 2000-329534 A | 11/2000 | | |
| JP | 2001-125009 A | 5/2001 | | |
| JP | 2001-272331 A | 10/2001 | | |
| JP | 2002-374034 A | 12/2002 | | |
| JP | 2003-143783 A | 5/2003 | | |
| JP | 2003-172690 A | 6/2003 | | |
| JP | 2003-256876 A | 9/2003 | | |
| JP | 2003-287534 A | 10/2003 | | |
| JP | 2005-274380 A | 10/2005 | | |
| JP | 2006-184284 A | 7/2006 | | |
| JP | 2006-266797 A | 10/2006 | | |
| JP | 2006-313158 A | 11/2006 | | |
| JP | 2007-024677 A | 2/2007 | | |
| JP | 2009-233001 A | 10/2009 | | |
| JP | 2011-56786 A | 3/2011 | | |
| SE | WO 2005053529 A1 * | 6/2005 | ............... | A61B 5/00 |
| WO | 91/01156 A1 | 2/1991 | | |
| WO | 92/16865 A1 | 10/1992 | | |
| WO | 93/06213 A1 | 4/1993 | | |
| WO | 93/08829 A1 | 5/1993 | | |
| WO | 98/38907 A1 | 9/1998 | | |
| WO | 98/57583 A1 | 12/1998 | | |
| WO | 00/11511 A1 | 3/2000 | | |
| WO | 00/44296 A1 | 8/2000 | | |
| WO | 01/11409 A2 | 2/2001 | | |
| WO | 03/062802 A2 | 7/2003 | | |
| WO | 03/073950 A1 | 9/2003 | | |
| WO | 2004/010856 A1 | 2/2004 | | |
| WO | 2004/023992 A1 | 3/2004 | | |
| WO | 2004/096049 A2 | 11/2004 | | |
| WO | 2005/047813 A1 | 5/2005 | | |
| WO | 2005/106695 A2 | 11/2005 | | |
| WO | 2006/029634 A2 | 3/2006 | | |
| WO | 2006/037132 A1 | 4/2006 | | |
| WO | 2006/039091 A2 | 4/2006 | | |
| WO | 2006/061829 A1 | 6/2006 | | |
| WO | 2006/068875 A2 | 6/2006 | | |
| WO | 2006/111704 A1 | 10/2006 | | |
| WO | 2006/119416 A2 | 11/2006 | | |
| WO | 2006/121851 A2 | 11/2006 | | |
| WO | 2006/130802 A2 | 12/2006 | | |
| WO | 2007/002685 A2 | 1/2007 | | |
| WO | WO 2007-025230 | 3/2007 | ............... | A61B 8/12 |
| WO | 2007/045690 A1 | 4/2007 | | |
| WO | 2007/058895 A2 | 5/2007 | | |
| WO | 2007/067323 A1 | 6/2007 | | |
| WO | 2007/084995 A2 | 7/2007 | | |
| WO | 2008/058084 A2 | 5/2008 | | |
| WO | 2008/069991 A1 | 6/2008 | | |
| WO | 2008/107905 A2 | 9/2008 | | |
| WO | 2009/009799 A1 | 1/2009 | | |
| WO | 2009/009801 A1 | 1/2009 | | |
| WO | 2009/046431 A1 | 4/2009 | | |
| WO | 2009/121067 A1 | 10/2009 | | |
| WO | 2009/137704 A1 | 11/2009 | | |
| WO | 2011/06886 A2 | 1/2011 | | |
| WO | 2011/038048 A1 | 3/2011 | | |
| WO | 2011/081688 A1 | 7/2011 | | |
| WO | 2012/003369 A2 | 1/2012 | | |
| WO | 2012/061935 A1 | 5/2012 | | |
| WO | 2012/071388 A2 | 5/2012 | | |
| WO | 2012/087818 A1 | 6/2012 | | |
| WO | 2012/098194 A1 | 7/2012 | | |
| WO | 2012/109676 A1 | 8/2012 | | |
| WO | 2012/130289 A1 | 10/2012 | | |
| WO | 2012/154767 A2 | 11/2012 | | |
| WO | 2012/155040 A1 | 11/2012 | | |
| WO | 2013/033414 A1 | 3/2013 | | |
| WO | 2013/033415 A2 | 3/2013 | | |
| WO | 2013/033418 A1 | 3/2013 | | |
| WO | 2013/033489 A1 | 3/2013 | | |
| WO | 2013/033490 A1 | 3/2013 | | |
| WO | 2013/033592 A1 | 3/2013 | | |
| WO | 2013/126390 A1 | 8/2013 | | |
| WO | 2014/109879 A1 | 7/2014 | | |

OTHER PUBLICATIONS

U.S. Appl. No. 60/949,472, filed Jul. 12, 2007, Kemp.
U.S. Appl. No. 61/051,340, filed May 7, 2008, Kemp.

(56) References Cited

OTHER PUBLICATIONS

Atlantis (TM) SR Pro Coronary Imaging Catheter 40 MHz Directions for Use, REF Catalog No. 38942 (published 2006), Boston Scientific Corporation, One Boston Scientific Place, Natick, MA 01760-1537 USA.
PCT International Search Report, pp. 1-3 (Oct. 1, 2009).
PCT Written Opinion, pp. 1-6 (Oct. 1, 2009).
European Search Report for 08796187.6 mailed Oct. 15, 2012, pp. 1-9.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.

(56) References Cited

OTHER PUBLICATIONS

International Search Report and Written Opinion mailed Nov. 2, 2012, for International Patent Application No. PCT/US12/53168, filed Aug. 30, 2013 (8 pages).
International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).
International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).
International Search Report and Written Opinion mailed on Feb. 28, 2014, for International Patent Application No. PCT/US13/75990, filed Dec. 18, 2013 (7 pages).
International Search Report and Written Opinion mailed on Jan. 16, 2009, for International Patent Application No. PCT/US08/78963 filed on Oct. 6, 2008 (7 pages).
International Search Report and Written Opinion mailed on Jul. 30, 2014, for International Patent Application No. PCT/US14/21659, filed Mar. 7, 2014 (15 pages).
International Search Report and Written Opinion mailed on Mar. 10, 2014, for International Patent Application No. PCT/US2013/076212, filed Dec. 18, 2013 (8 pages).
International Search Report and Written Opinion mailed on Mar. 11, 2014, for International Patent Application No. PCT/US13/76173, filed Dec. 16, 2013 (9 pages).
International Search Report and Written Opinion mailed on Mar. 11, 2014, for International Patent Application No. PCT/US13/76449, filed Dec. 19, 2013 (9 pages).
International Search Report and Written Opinion mailed on Mar. 18, 2014, for International Patent Application No. PCT/US2013/076502, filed Dec. 19, 2013 (7 pages).
International Search Report and Written Opinion mailed on Mar. 18, 2014, for International Patent Application No. PCT/US2013/076788, filed Dec. 20, 2013 (7 pages).
International Search Report and Written Opinion mailed on Mar. 19, 2014, for International Patent Application No. PCT/US13/75349, filed Dec. 16, 2013 (10 pages).
International Search Report and Written Opinion mailed on Mar. 19, 2014, for International Patent Application No. PCT/US2013/076587, filed Dec. 19, 2013 (10 pages).
International Search Report and Written Opinion mailed on Mar. 19, 2014, for International Patent Application No. PCT/US2013/076909, filed Dec. 20, 2013 (7 pages).
International Search Report and Written Opinion mailed on Mar. 7, 2014, for International Patent Application No. PCT/US2013/076304, filed Dec. 18, 2013 (9 pages).
International Search Report and Written Opinion mailed on Mar. 7, 2014, for International Patent Application No. PCT/US2013/076480, filed Dec. 19, 2013 (8 pages).
International Search Report and Written Opinion mailed on Mar. 7, 2014, for International Patent Application No. PCT/US2013/076512, filed Dec. 19, 2013 (8 pages).
International Search Report and Written Opinion mailed on Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.

(56) References Cited

OTHER PUBLICATIONS

Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley—Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).
Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.

(56) References Cited

OTHER PUBLICATIONS

Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.

\* cited by examiner

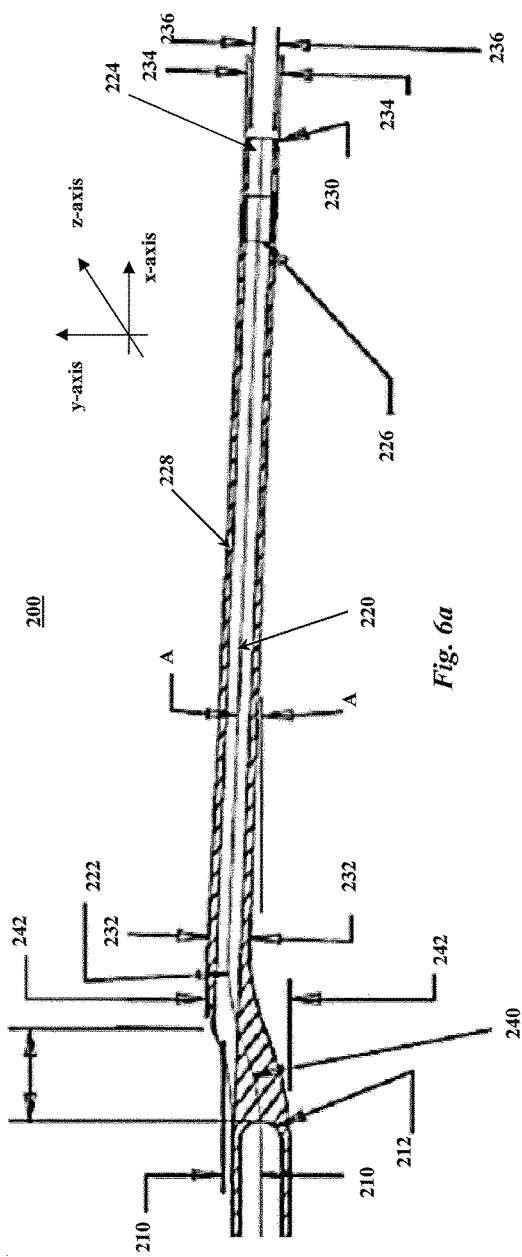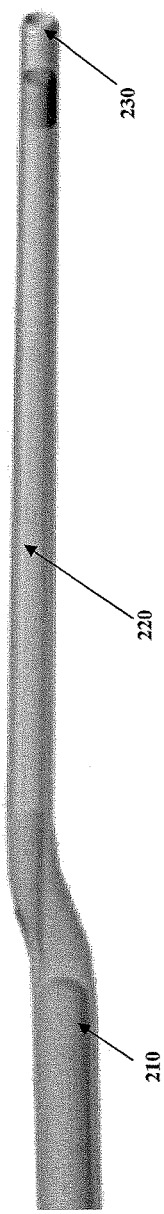
Fig. 6a
Fig. 6b

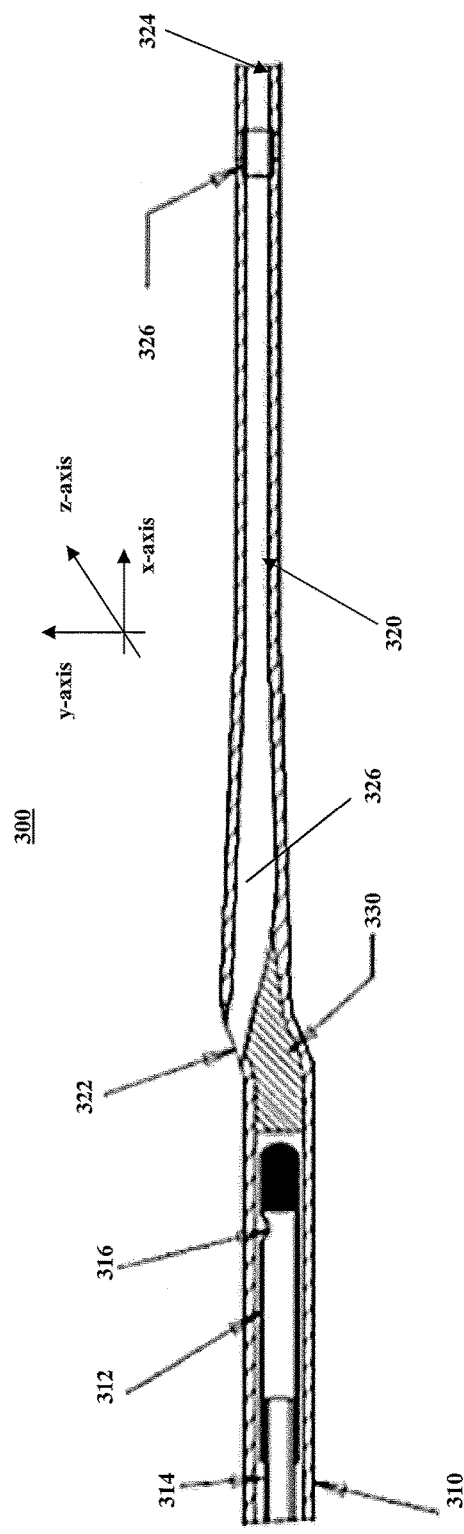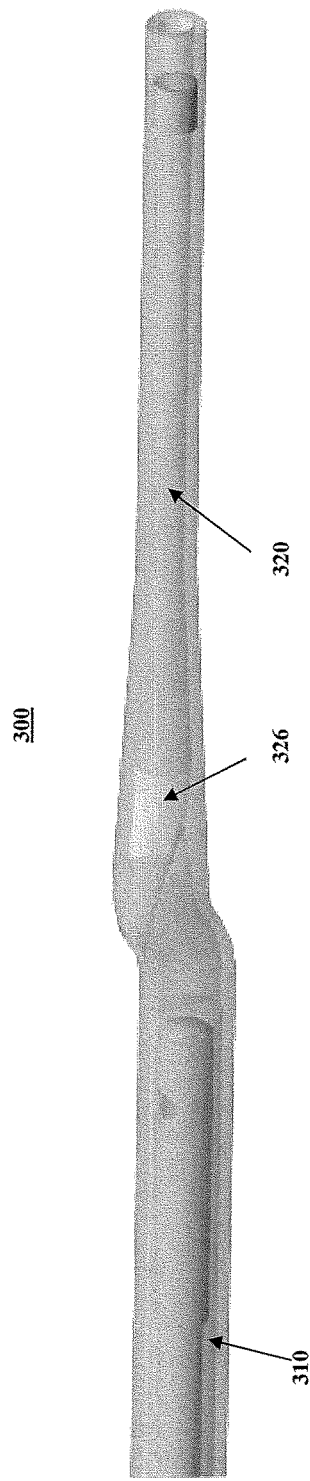
Fig. 8a
Fig. 8b

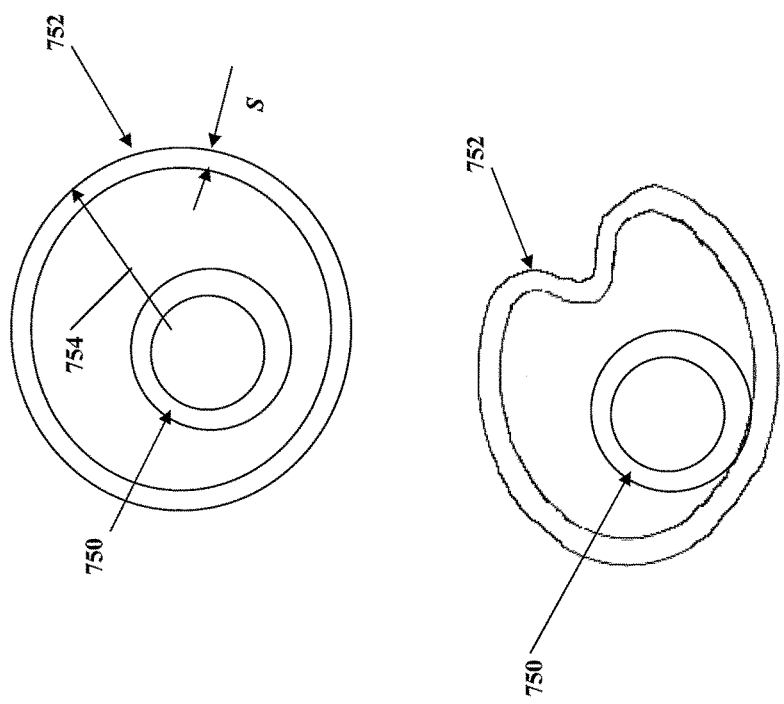

CATHETER FOR IN VIVO IMAGING

CROSS-RELATED APPLICATIONS

The present application claims priority to U.S. Provisional Application Ser. No. 60/949,511, filed Jul. 12, 2007, incorporated by reference herein.

BACKGROUND OF THE INVENTION

The present invention relates generally to an apparatus for in vivo imaging. More particularly, the present invention pertains to a catheter for imaging within a mammalian body, including luminal systems, such as imaging the vasculature system, including, without limitation, cardiac vasculature, peripheral vasculature and neural vasculature.

For intravascular imaging, it is difficult to achieve and maintain a uniform rotational velocity due to cables and shafts binding and/or whipping around as it is rotated in the blood vessel. Intravascular probes rotate at a nonuniform angular velocity even though the motor rotates at a uniform angular velocity. This is a problem because the angles assumed by the image processor in assembling the image vectors into the cross-sectional image of the body lumens are different from the actual angles at which the image vectors were taken. This causes the cross-sectional image of the blood vessel to be distorted in the azimuthal and radial direction. The resulting distortion is referred as Nonuniform Rotational Distortion ("NURD"). The embodiments disclosed herein attempt to solve these problems, as well as others.

SUMMARY OF THE INVENTION

The foregoing and other features and advantages are defined by the appended claims. The following detailed description of exemplary embodiments, read in conjunction with the accompanying drawings is merely illustrative rather than limiting, the scope being defined by the appended claims and equivalents thereof.

A catheter for in vivo imaging comprising a monolithic outer sheath terminating in a monolithic atraumatic tip having a guidewire lumen passing through the monolithic atraumatic tip. The catheter for in vivo imaging comprises a rotary drive shaft that passes through a central lumen of the catheter monolithic outer sheath to impart rotary motion.

BRIEF DESCRIPTION OF THE DRAWINGS

The foregoing description of the figures is provided for a more complete understanding of the drawings. It should be understood, however, that the embodiments are not limited to the precise arrangements and configurations shown.

FIG. 6a is a cross-sectional schematic view of one embodiment of the catheter monolithic outer sheath; and FIG. 6b is a perspective view of one embodiment of the catheter monolithic outer sheath depicting the sheath lumen and the guidewire lumen and sheath lumen in phantom FIG. 8a is a cross-sectional schematic view of one embodiment of the catheter monolithic outer sheath; and FIG. 8b is a perspective view of one embodiment of the catheter monolithic outer sheath depicting the guidewire lumen and the optical train in phantom.

FIG. 16a shows the catheter in a straight vessel where the NURD is small; FIG. 16b shows the catheter the NURD mask in a sharp 90 bend in the distal end where the NURD is small; and FIG. 16c shows the catheter in a tortuous model LAD Co-Pilot within a tight valve and small NURD values.

FIG. 20a is a cross section of the outer wall of the stationary sheath including a thickness S; and FIG. 20b is the cross section of the outer wall of the stationary sheath with a geometrical image distortion when NURD is present.

DETAILED DESCRIPTION OF THE PREFERRED EMBODIMENTS

The methods, apparatuses, and systems can be understood more readily by reference to the following detailed description of the methods, apparatuses, and systems, the non-limiting embodiments, and the accompanying figures.

Figure 1:
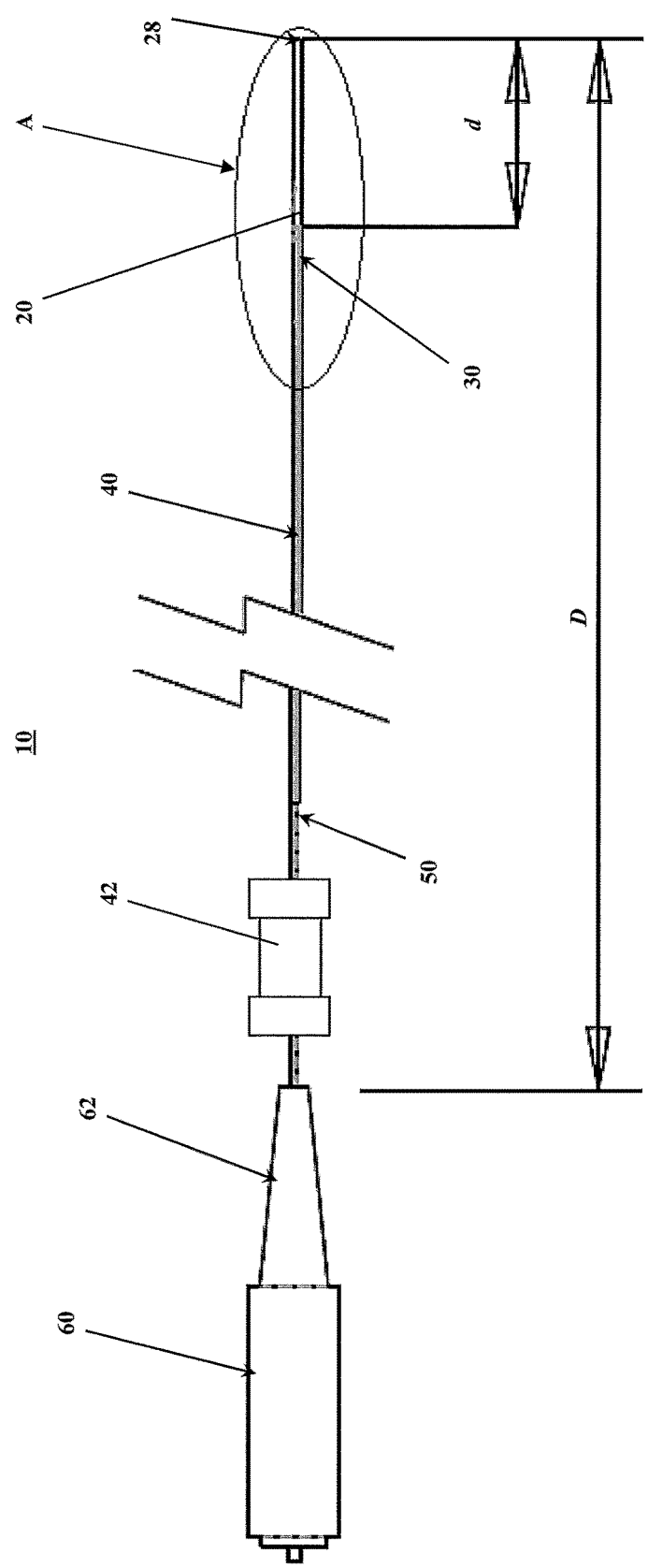
FIG. 1 is a partial fragmentary view of the imaging catheter in accordance with one embodiment.

With particular reference to FIG. 1, a catheter 10 is depicted comprising a monolithic outer sheath 20 including a central sheath lumen extending substantially the entire length of the monolithic outer sheath 20 and a monolithically formed flexible tip 28. The term "monolithic" or "monolithically formed" is without any joints or junctions formed by thermal, chemical or mechanical bonding.

The catheter 10 construct for in vivo imaging, particularly, imaging of anatomical passageways, such as cardiovascular, neurovascular, gastrointestinal, genitor-urinary tract, or other anatomical luminal structures. The catheter 10 is coupled to an imaging modality, and in one embodiment the imaging modality is an Optical Coherence Tomography ("OCT") system. OCT is an optical interferometric technique for imaging subsurface tissue structure with micrometer-scale resolution. In another embodiment, the imaging modality is an ultrasound imaging modality, such as intravascular ultrasound ("IVUS), either alone or in combination with OCT imaging. The OCT system may include tunable laser or broadband light source or multiple tunable laser sources with corresponding detectors, and may be a spectrometer based OCT system or a Fourier Domain OCT system, as disclosed in U.S. Provisional Application 60/949,467, herein incorporated by reference. The catheter 10 may be integrated with IVUS by an OCT-IVUS catheter for concurrent imaging, as described in U.S. Provisional Application 60/949,472, herein incorporated by reference. As shown in FIG. 1, the catheter 10 comprises the monolithic outer sheath 20 that houses an acoustical or optical train 30. The optical train 20 includes a length of d, and the catheter 10 includes a length of D from the distal portion of the FORJ 60 to the distal monolithic tip 28 of the catheter monolithic outer sheath 20. In use, the optical train 30 rotates under the influence of an external rotary drive motor (not shown) coupled to a rotary drive shaft 40 and an optical fiber 50 through a Fiber Optic Rotary Junction 60 ("FORJ"), thereby also rotating the optical train 30. The rotary drive shaft 40 includes a drive shaft lumen, through which the optical fiber 50 is concentrically or coaxially disposed.

As shown in FIG. 1, a plug-in connector 62 is coupled to the proximal end of the rotary drive shaft 40, to couple the catheter 10 to the rotary drive motor. The plug-in connector may include a Subscription Channel (SC)—Angled Physical Contact (APC) connectors to ensure lower insertion loss and back reflection. The FORJ 60 may include fiber pigtail, ST, FC, SC, FC/UPC receptacles, or any combination receptacles on the rotor or the stator side (Princetel, Lawrenceville, N.J.). Alternatively, the connector 62 may include a centering boot to center the optical fiber with respect to the rotary drive shaft 40. The centering boot includes a first lumen to accept the optical fiber and a second lumen to accept the rotary drive shaft 40. The FORJ is provided to permit rotation of the optical fiber and rotary shaft while maintaining optical communication with the radiant light source (e.g., tunable laser or broadband emitter) with minimal insertion loss and return loss performance. The rotary drive motor imparts rotational movement to the rotary drive shaft 40 either by a DC brushless motor and the like. The rotary drive motor may rotate at revolutions per minute (RPM) for a 360 degree rotation of the rotary drive shaft 40.

A linear pull back mechanism may also be coupled to the rotary drive shaft, which may include a stepping motor. The monolithic outer sheath 20 is held stationary, relative to the rotary drive shaft 40, by use of a permanently affixed retaining bead 42 that is connected to the frame of the rotary drive motor. The bead includes a first lumen and a second lumen smaller than the first lumen, whereby the second lumen communicates through the first lumen. In one embodiment, the bead is a single machined aluminum part that is attached to the monolithic outer sheath 20 by means of mechanical thread engagement and adhesive.

The rotary drive shaft 40 is concentrically or coaxially positioned within the central lumen of the monolithic outer sheath 20 and substantially extends along the longitudinal length D of the central lumen. Coaxially engagement between the rotary drive shaft 40 and the central lumen of the monolithic outer sheath 20 may be accomplished with the OD of the rotary drive shaft 40 matching the ID of the monolithic outer sheath 20 or varying the OD of the rotary drive shaft to the ID of the monolithic outer sheath 20. The rotary drive shaft 40 terminates at its distal end in proximity to the distal end of the central lumen adjacent the proximal end of the catheter 10. The optical train 30 is carried by the rotary drive shaft 40, with the optical fiber 50 running the length of the rotary drive shaft 40 through the drive shaft lumen. The rotary drive shaft 40 permits transmission of torque from the rotary motor to the optical train 30 along the entire length of the catheter shaft. As such, the rotary dive shaft 40 includes having sufficient torsional rigidity or torqueability and lateral flexibility or flexion to navigate potentially tortuous anatomical pathways while minimizing NURD to ensure accurate imaging. Torqueability is the ability of the rotary drive shaft to be turned or rotated while traversing bends or turns in the patient's vasculature.

In one embodiment, the rotary drive shaft 40 includes a hypotube metal over a proximal portion or the entire proximal section of the rotary drive shaft 40. Alternatively, the rotary drive shaft 40 includes a stranded hollow core shaft extending the substantial length of the rotary drive shaft 40. The stranded hollow core shaft may comprise a plurality of helically wound wire strands so that mechanical rotation of the rotary drive shaft is in the same direction as the helical wire strands. The stranded hollow core shaft may include an inner stranded drive shaft and outer stranded drive shaft, where in outer stranded drive shaft is wound in the opposite helical direction than the inner stranded drive shaft. A protection bearing 70 may be coupled to either the stranded hollow core shaft or the hypotube metal. The stranded hollow core shaft, the hypotube metal, or a combination thereof provides sufficient lateral flexibility to ensure access through highly tortuous passageways, such as the aortic arch and coronary arteries. In another embodiment, the hypotube metal is concentrically or coaxially fitted over a proximal portion or the entire proximal section of the stranded hollow core shaft. The coaxial fitting of the hypotube metal over the stranded hollow core shaft may be accomplished by allowing the OD of the stranded hollow core shaft to vary from the ID of the hypotube metal tube by about 0.001 to 0.009 inches. In this manner the highly flexible stranded hollow core shaft lessens NURD by the relatively less flexible hypotube metal at the more distal end of the catheter to permit greater distal end flexion or lateral flexibility. While maintaining flexibility, the rotary drive shaft also maintains the pushability, the ability of the catheter to be efficiently and easily pushed through the vasculature of the patient without damage to the catheter or patient, getting blocked, kinked, whipped, etc.

In accordance with another embodiment, the rotary drive shaft 40 includes a shortened hypotube metal shaft attached in a generally overlapping attachment with a section of stranded hollow core shaft, with there being a very slight mismatch in the outer diameters between the hypotube metal and the stranded hollow core shaft to permit concentric or coaxial engagement and attachment between the respective end sections. Alternatively, the hypotube metal and the stranded hollow core shaft may have generally the same outer diameter to permit end-to-end connection, such as a butt weld there between. The stranded hollow core shaft includes single layer uni-directional and multi-layer directional winding configurations when coupled to the hypotube metal shaft.

In one embodiment of the monolithic outer sheath 20, at least a portion of the monolithic outer sheath is fabricated of an optically transparent polymer, such as, for example, perfluoroalkoxy (PFA) polymer, polytetrafluoroethylene (PTFE) partially covered with a polyether block amide (Pebax®) at the distal end, or tetrafluoroethylene and hexafloropropylene co-polymer (FEP). The optically transparent polymer is transparent in the spectral region of light being used for imaging. Similar biocompatible optically transparent polymers having similar properties of lubricity, flexibility, optical clarity, biocompatible and sterilizability may alternatively be employed to form the catheter shaft. In accordance with one embodiment, FEP is used to fabricate the catheter sheath. The catheter sheath is fabricated in a monolithic manner such that the central lumen terminates at the atraumatic monolithic tip without any intervening joints. Atraumatic is not producing injury or damage. As shown in FIG. 2b, a rapid exchange guidewire lumen 22 is formed entirely within the atraumatic monolithic tip with both the proximal guidewire port and the distal guidewire port accessing the guidewire lumen distal the termination of the central lumen of the catheter sheath. The guidewire is the thin wire over which the catheter rides.

Figure 2A:
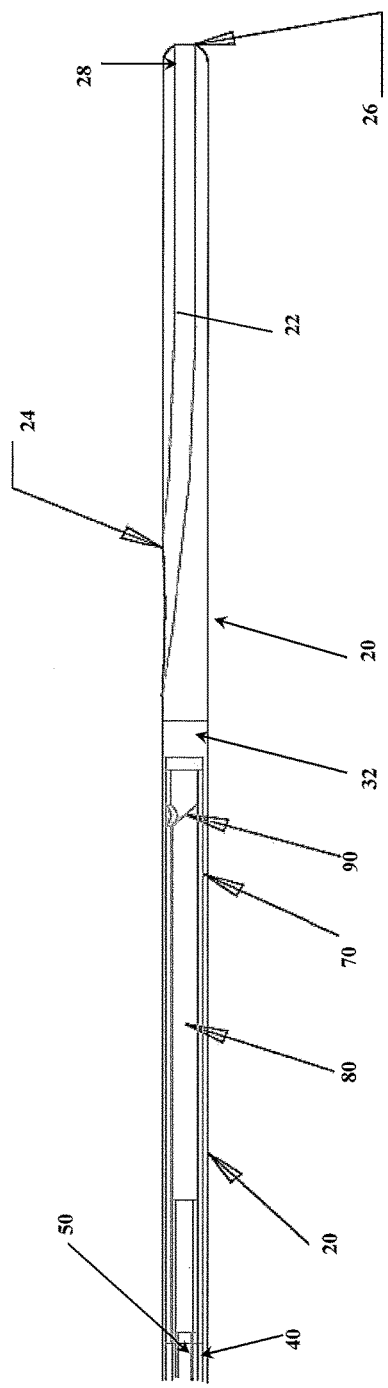
FIG. 2a is an enlarged portion of A of FIG. 1, showing the distal end of the OCT imaging catheter in accordance with one embodiment.
Figure 2B:
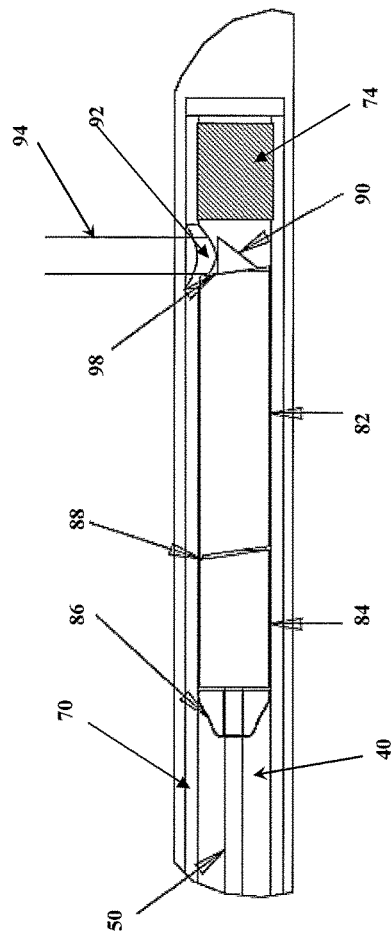
FIG. 2b is a cross-sectional view of the optical train.

As shown in FIG. 2a, a guidewire lumen 22 is formed in the distal portion of the monolithic outer sheath 20, while a central sheath lumen 32 extends proximally from the distal portion of the monolithic outer sheath 20. The guidewire lumen 22 includes a guidewire exit 24 and a guidewire entrance 26. The guidewire lumen 22 is positioned entirely in the distal terminus of the central sheath lumen 32 such that the guidewire (not shown) may be rapidly exchanged and does not interfere with the rotational movement of the optical train 30, rotary drive shaft 40 or the protection bearing 70 within the central lumen of the catheter sheath 20.

In accordance with a another embodiment, the rotary drive shaft 40 includes the protection bearing 70, which houses the distal end optics or distal end acoustics at the distal end of the catheter 10, as shown in FIG. 2b. The protection bearing 70 may be coaxially mounted over the distal end optics, or alternatively, molded over the distal end optics or the distal end optics molded into the protection bearing 70. The protection bearing 70 may include a diameter to coaxially engage the distal end optics to ensure a 1:1 rotation of the protection bearing 70 with the distal end optics. In one embodiment, the protection bearing 70 may include a Platinum/Iridium tube and is formed with an opening 92. The opening may be positioned in optical alignment with the prism 90 in order to permit light to pass through the opening 92 and optically communicate with the sample being imaged, as shown in FIG. 2b. The Platinum/Iridium tube may comprise about 75-97% Pt and about 3-25% Ir, which provides radiopacity. Alternatively, the metal hypotube of the rotary drive shaft replaces the protection bearing 70, where the metal hypotube extends coaxially over the distal end optics and includes an opening for the distal end optics. Alternatively, the protection bearing 70 may include other metals nitinol, i.e. nickel titanium alloy, or another pseudometallic biocompatible alloy such as stainless steel, tantalum, gold, platinum, titanium, copper, nickel, vanadium, zinc metal alloys thereof, copper-zinc-aluminum alloy, and combinations thereof, with radiopaque markers in order to provide visible reference points. Alternatively, the protection bearing 70 may include an epoxy rounded tip to ensure smooth rotational translation of the protection bearing 70. Alternatively, the protection bearing 70 includes a bearing plug 74 within the distal portion of the protection bearing's distal lumen. The bearing plug 74 may coaxially fit into the distal portion of the protection bearing 70, or may be secured by adhesive, welding, and the like. The bearing plug 74 may include a metal material, alternatively a metal/polymer material, alternatively stainless steel.

In accordance with one embodiment, the optical train 30 includes the monolithic outer sheath 20 the optical fiber 50 in association with the rotary drive shaft 40, the protection bearing 70 housing a ferrule/gradient index lens ("GRIN") assembly 80 at a distal end of the optical fiber 50, as shown in FIG. 2a. The ferrule/GRIN assembly 80 optically coupled to a prism 90 or mirror to conduct light between the optical fiber 50, ferrule/GRIN assembly and the sample being imaged. The distal end of the optical train 30, i.e., the distal end optical fiber 50, the ferrule/GRIN lens assembly and the prism 90, are all secured within the protection bearing 70 and rotate with the protection bearing 70, under the influence of the rotary drive shaft 40, within the central lumen 32 of the catheter sheath 20. In use, the optical train 30 rotates under the influence of an external rotary drive motor coupled to the rotary drive shaft and optical fiber through the FORJ 60, thereby also rotating the ferrule/GRIN lens 80 assembly and the prism 90 to emit optical energy 94 at an angle and through 360 degrees around the monolithic outer sheath 20.

As shown in FIG. 2b, the ferrule/GRIN assembly 80 includes a GRIN lens 82 and a ferrule 84. The optical fiber 50 may include a core, cladding and buffer and is optically coupled to the ferrule 84. The ferrule 84 is optically coupled to the GRIN lens 82 and prism 90 to transmit light between the optical fiber 50, GRIN lens 82 and the sample being imaged. The ferrule 84 at a distal end of the optical fiber 50 supports and terminates the distal end of the optical fiber 50, where the optical fiber 50 may be coaxially fitted within the ferrule 84. The ferrule may include a lumen and a tapered cladding to coaxially couple the core of the optical fiber 50. When the optical fiber 50 core is coupled with the ferrule 84, the fiber 50 may not include the buffer. The optical fiber 50 may be potted or adhesively secured to the ferrule 84 at point 86 with optical glue, curing adhesive, and the like, as to provide a coaxial alignment of the optical fiber and the ferrule. The GRIN lens 82 is optically coupled to a distal surface of the ferrule 84 at point 88, such as by optically transparent adhesive. The GRIN lens 82 and the ferrule 84 may include an angled engagement, where the angle offset of the distal end of the ferrule 84 matches the angle offset of the proximal end of the GRIN lens 82. The prism or mirror 90 is optically coupled to the distal surface of the GRIN lens 82 at point 98, such as by optically transparent adhesive. The distal surface of the GRIN lens 82 may include an angled offset. The prism 90 may include a right angled prism and the prism angles may be constructed to provide balancing of astigmatism introduced by the sheath. An optical pathway is formed along the longitudinal axis of the rotary drive shaft 40, the catheter sheath 20, and protection bearing 70. The prism or mirror 90 serves to redirect at least some portion of the light away from the central longitudinal axis and generally radially outward, through the optically transparent portion of the monolithic outer sheath 20 to communicate with the body tissue being imaged throughout 360 degrees.

Some of the incident light may not be redirected radially outward. The prism angles may be constructed to provide a balancing of astigmatism introduced by the catheter sheath. The incident light may not necessarily all be used for imaging, where additional optical energy beams are for therapeutic purposes or possibly some other energy source, as disclosed in commonly assigned application entitled "Method and Apparatus for Simultaneous Hemoglobin Reflectivity Measurement and OCT Scan of Coronary Arteries, Thrombus Detection and Treatment, and OCT Flushing" Ser. No. 61/040,630, filed Mar. 28, 2008, herein incorporated by reference. Alternatively, the catheter may include an air-filled sheath, as described in commonly assigned provisional application Ser. No. 61/051,340, filed May 7, 2008, incorporated by reference herein.

Catheter Sheath

Figure 3A:
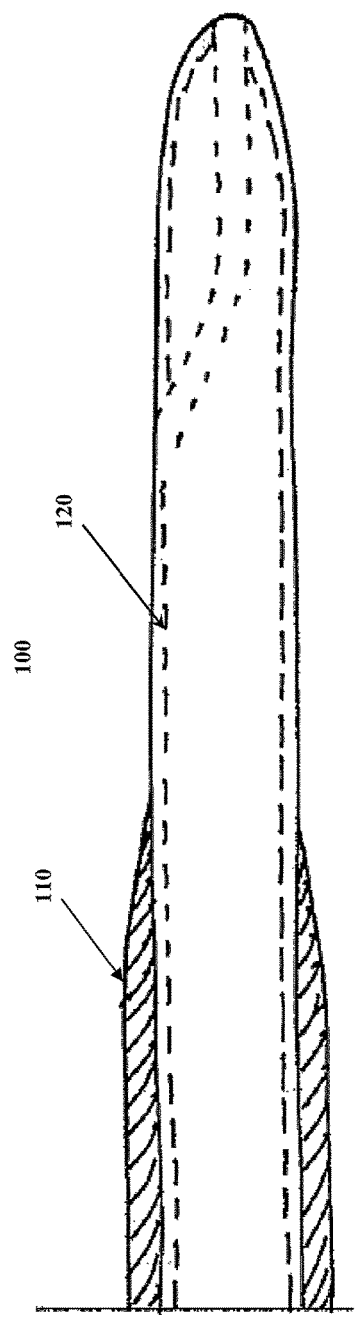
FIG. 3a is a side elevational, cross-sectional view of an embodiment of the monolithic distal tip and guidewire lumen of a monolithic catheter sheath.
Figure 3B:
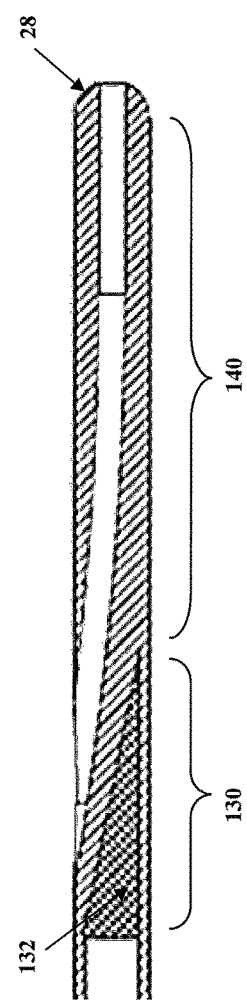
FIG. 3b is a side elevational, cross-sectional view of one embodiment of the monolithic catheter sheath.

As shown in FIG. 3a, one embodiment of the monolithic outer sheath 20 may include an outer layer 110 and an inner layer 120 to form a laminate structure 100. The outer layer 110 may be constructed of Pebax® extending the substantial length along the proximal portion of the catheter sheath and the outer layer 110 provides greater structural rigidity relative to the inner layer 120. The inner layer 120 may be constructed of PTFE, with the PTFE inner layer 120 extending distally from the Pebax® outer layer 110 and forming the most distal section, which is optically transparent and flexible to permit optical communication to the sample and greater traversability for the catheter during insertion or retraction within the anatomical passageway. Alternatively, various other materials, such as FEP, could be used in place of PTFE in the given example. FIG. 3b shows the solid monolithically formed tip 28 and a base layer 130 and a top layer 140. The base layer 130 may be constructed of Pebax® substantially along the base of the catheter sheath and provides greater structural rigidity relative to the top layer 140. The greater structural rigidity allows the monolithic outer sheath greater pushability along the proximal portion of the monolithic outer sheath. Alternatively, the base layer 130 may include a plug 132. The plug 132 may include a space between the protection bearing 70 when the protection bearing 70 engages with the monolithic outer sheath 20. The plug 132 may include an angled engagement with distal portion of the sheath lumen to impart increased flexibility to the distal end of the monolithic outer sheath 20. The plug 132 may include polymeric material, including, but not limited to PTFE, FEP, and the like. The top layer 140 may be constructed of PTFE, with the PTFE top layer 140 extending distally from the Pebax® base layer 130, which provides greater flexibility along the distal end of the monolithic outer sheath for navigating tortuous pathways. Alternatively, the layers of the monolithic sheath 20 include a coating either on the outer layers or inner layers for smooth transitioning and less friction during navigation. Such coatings may be biocompatible, polymeric, saline, and the like.

Figure 4:
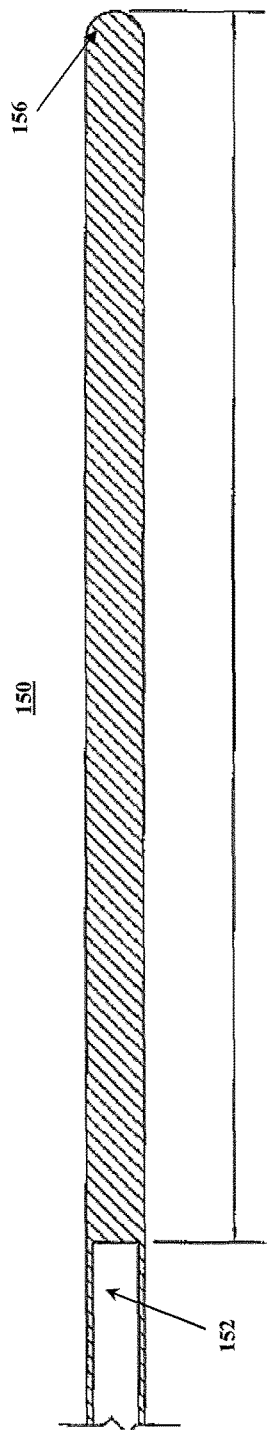
FIG. 4 is a side, cross-sectional view of a distal end of one embodiment of the monolithic catheter sheath prior to forming the guidewire lumen.

FIG. 4 depicts the monolithic outer sheath 20 prior to the guidewire lumen 22 being formed. In one embodiment, the solid monolithically formed tip 28 is formed by first providing a tubular catheter sheath precursor 150, preferably placing a forming mandrel in the central sheath lumen 152 of the tubular catheter sheath precursor 150, then thermoforming the solid tip 154 into a desired shape. Thermoforming is any process of forming thermoplastic sheet, which consists of heating the sheet and forcing it onto a mold surface. The sheet or film is heated between infrared, natural gas, or other heaters to its forming temperature, then it is stretched over or into a temperature-controlled, single-surface mold. The sheet is held against the mold surface unit until cooled, and the formed part is then trimmed from the sheet. There are several categories of thermoforming, including vacuum forming, pressure forming, twin-sheet forming, drape forming, free blowing, simple sheet bending, and the like. The shape of the monolithic tip 28 may be rounded, radiused, tapered, or generally frustroconical with an atraumatic distal end formed. A radiused tip includes an angle of curvature that is derived from the radius of the outer sheath OD, where the angle or degree of curvature equals the reciprocal of the radius (1/R).

Figure 5:
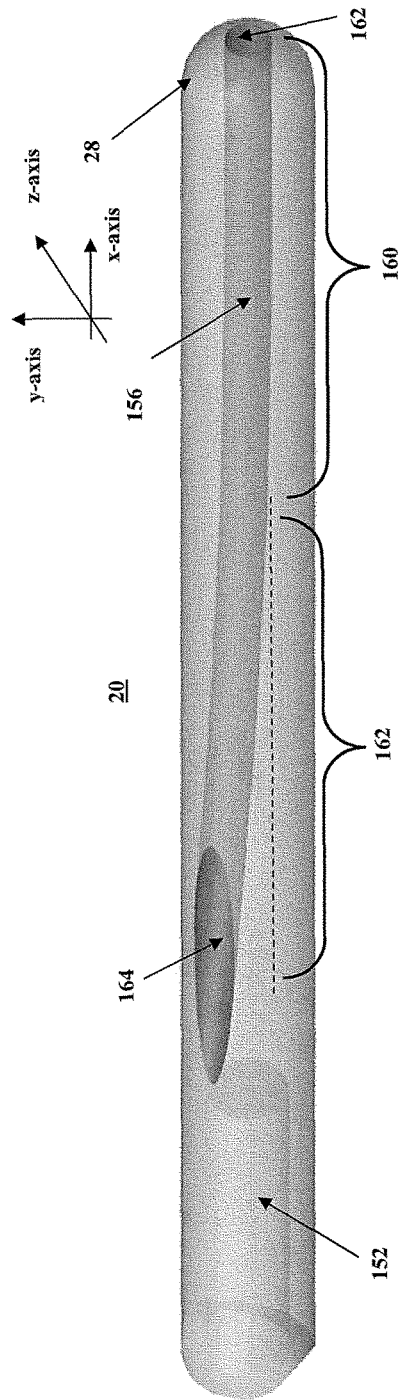
FIG. 5 is a perspective view of the monolithic catheter sheath depicting the sheath lumen and the guidewire lumen in phantom.

The guidewire lumen 156, as shown in phantom depicted in FIG. 5 may then be formed by bending the solid distal tip 28 and drilling a straight hole angularly through the distal end and to a lateral side of the distal tip, then releasing the bend in the tip to provide distal end and proximal side guidewire ports and a curved lumen. Alternatively, the tip may be formed with the guidewire lumen 156 during the thermoforming process by providing the appropriate mold. The resulting guidewire lumen 156 may or may not maintain a straight longitudinal axis, where the longitudinal axis runs along the x-axis of the sheath 20, as shown in phantom in FIG. 5. In one embodiment, the guidewire lumen 156 includes a straight longitudinal axis 160 and a non-longitudinal axis 162. The straight longitudinal axis 160 is included for some length along the distal portion of the catheter sheath body and associated with the guidewire entrance 162. The non-longitudinal axis 162 is included for some length along the proximal portion of the catheter body and is associated with the guidewire exit 164. The angled measurements for the non-longitudinal axis 162 near the guidewire exit can be any angle relative to the longitudinal axis 160 as to provide for the rapid exchange of the guidewire and no kinking or whipping of the guidewire. In one embodiment, the angle or degree of curvature for the non-longitudinal axis relative the longitudinal axis is about 0.1 to 10 degrees, about 1 to 8 degrees, or about 1.5 to 6 degrees.

The monolithic outer sheath 20 includes the absence of or potential for uneven surfaces that may irritate or damage tissues in anatomical passageways or interfere with the guiding catheter during retraction or advancement of the catheter, the absence of joints which could separate and dangerously embolize, and the absence of joints which could leak fluid into or out of the sheath. Because of its monolithic construction, the central lumen of the outer catheter sheath may be filled with a fluid that could serve to (a) provide lubrication between the monolithic outer sheath and the rotary shaft, (b) reduce optical astigmatism originating from the cylindrical curvature of the inner sheath surface due to the lower index of refraction mismatch of liquid when compared with air, (c) provide additional column strength and kink resistance to the catheter, (d) viscously dampen NURD, or (e) provide negative torsional feedback to stabilize or dampen non-uniformities in rotation.

The monolithic design of the catheter outer sheath and the monolithic atraumatic tip further permit different engineering of material properties along the length of the monolithic outer sheath. For example, the durometer of the catheter sheath may be varied along the length of the catheter sheath during manufacture of the sheath precursor material; the inner and/or outer diameter of the catheter sheath may be made to vary, such as by tapering, along the length of the continuous monolithic tube; the wall thicknesses of the catheter sheath and the concomitant flexibility profiles may be varied along the longitudinal length of the catheter sheath, or the catheter sheath may be variably reinforced to alter the flexibility profiles along the longitudinal axis of the catheter sheath, such as by applying a braiding material, a concentric reinforcement, such as another overlaid tube, or combinations of the foregoing. The braiding material may be a polymer formed from conventional braiding machines. The durometer is the hardness of the material, as defined as the material's resistance to permanent indentation. The two most common scales, using slightly different measurement systems, are the ASTM D2240 type A and type D scales. The A scale is for softer plastics, while the D scale is for harder ones. However, the ASTM D2240-00 testing standard calls for a total of 12 scales, depending on the intended use; types A, B, C, D, DO, E, M, O, OO, OOO, OOO-S, and R. Each scale results in a value between 0 and 100, with higher values indicating a harder material.

Another embodiment of the monolithic catheter sheath 200 is shown in FIG. 6a. The monolithic catheter sheath 200 includes a sheath lumen 210, a guidewire lumen 220, and a monolithic atraumatic tip 230. The sheath lumen 210 includes a rounded distal end 212 for the placement of the optical train 30. The sheath lumen 210 includes a longitudinal axis substantially along the x-axis direction of the monolithic catheter sheath 200. The guidewire lumen 220 includes a guidewire exit 222, a guidewire entrance 224, and a distal marker band 226. The distal marker band 226 is of a radiopaque material. The guidewire lumen 220 includes a diameter 236, which may remain constant along the longitudinal length of the guidewire lumen 220. The longitudinal axis of the guidewire lumen 210 is at a slight angle A and offset from the longitudinal axis of the sheath lumen 210. The offset angle A may be about 1 to 20 degrees, from about 1 to 5 degrees, and from about 2 to 4 degrees The offset angle A minimizes space between the guidewire and the catheter body, which helps to minimize chance of the guidewire getting entangled when crossing stents. The catheter sheath 200 also includes a buffer 240 of solid material between guide wire lumen 220 and the sheath lumen 210 to prevent the passage of fluid and offset the guidewire lumen 220 from the sheath lumen 210. The guide wire lumen 220 is approximately straight along its longitudinal axis, as to permit free passage of guide wire (not shown). The guidewire lumen 200 includes a guidewire lumen wall 228 that includes at least two thicknesses. In one embodiment, the guidewire lumen wall 228 includes a first thickness 232 near the guidewire exit 222 slightly larger than a second thickness 234 near the guidewire entrance 224. The guidewire lumen wall 228 first thickness near guidewire exit 222 evenly distributes strain on the monolithic catheter sheath 200 and prevents kinking of the guidewire at the guidewire exit 222. An outer transparent view of the monolithic catheter sheath 200 is shown in FIG. 6b, showing the sheath lumen 210 and guidewire lumen 220 in phantom.

Figure 7A:
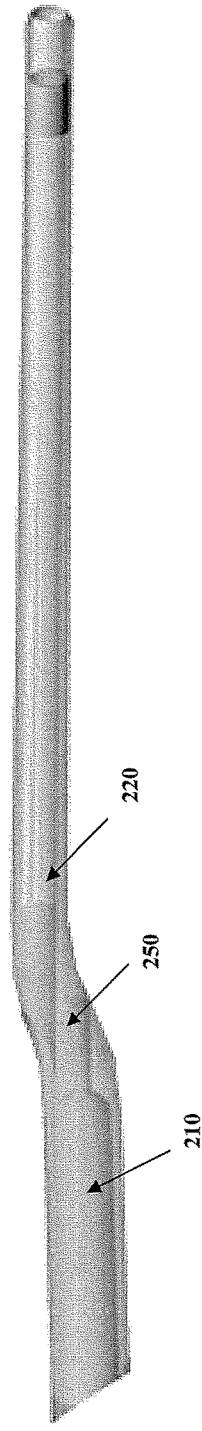
FIG. 7a is a perspective view of one embodiment of the catheter monolithic outer sheath depicting the sheath lumen and the guidewire lumen in phantom.
Figure 7B:
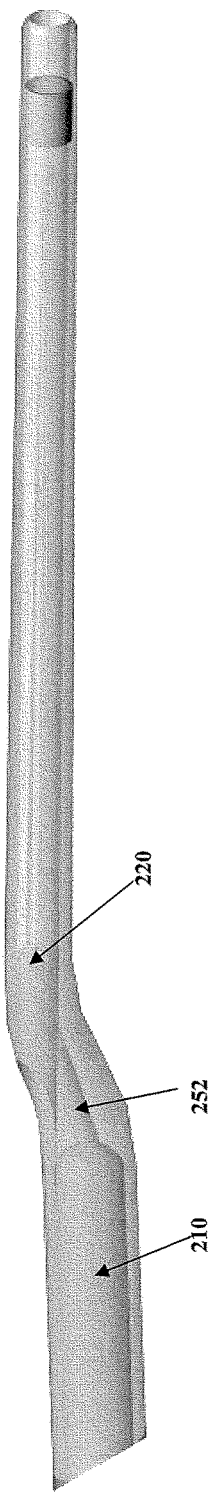
FIG. 7b is a perspective view of one embodiment of the catheter monolithic outer sheath depicting the sheath lumen and the guidewire lumen in phantom

As shown in phantom in FIG. 7a, in another embodiment of the monolithic catheter sheath 200, a flushing port 250 is coupled to the sheath lumen 210 and the exterior of the catheter sheath 200. The flushing port 250 between the sheath lumen 210 and the exterior of the catheter sheath 200 allows an operator to flush air or any fluid out of the sheath lumen 210. The monolithic catheter sheath 200 may use standard luer connections at the proximal end of the catheter sheath 200 to provide the flushing fluid. Luer connection systems are the standard way of attaching catheters, IV tubes, and so on to each other, and they consist of round male and female interlocking tubes, slightly tapered to hold together better with even just a simple pressure/twist fit. Luer connections can either be a luer slip, or can have an additional outer rim of threading. Alternatively, the embodiment of the monolithic catheter sheath 200 includes a flushing port 252 coupled to the guidewire lumen 220 and the sheath lumen 210 to allow the operator to flush air or fluid out of the sheath lumen 210, as shown in phantom in FIG. 7b.

Another embodiment of the monolithic catheter sheath 300 is shown in FIG. 8a. The monolithic catheter sheath 300 includes a sheath lumen 310, a guidewire lumen 320, and a plug 330. The sheath lumen 310 includes a longitudinal axis substantially along the x-axis of the monolithic catheter sheath 300. The sheath lumen 310 houses the protection bearing 312 coupled to the drive shaft 314 and the OCT imaging port 316. The guidewire lumen 320 includes a guidewire exit 322, a guidewire entrance 324, and a curvature 326 offset lumen. The distal portion of the guidewire lumen 320 includes a longitudinal axis along the x-axis of the catheter sheath 300. The catheter sheath 300 also includes a plug 330 of solid material between guidewire lumen 320 and the sheath lumen 310 to prevent the passage of fluid and offset the guidewire lumen 320 from the sheath lumen 310. The curvature lumen 326 is offset from the distal longitudinal axis of the guidewire lumen and the longitudinal axis of the sheath lumen 310. The curvature 326 offset minimizes space between the guidewire (not shown) and the monolithic catheter body, which helps to minimize the wire entangling when crossing stents and tortuous pathways. An outer transparent view of the monolithic catheter sheath 300 embodiment is shown in FIG. 8b, with the sheath lumen 310, the guidewire lumen 320, and the curvature lumen 326 in phantom.

Rotary Drive Shaft

Figure 9A:
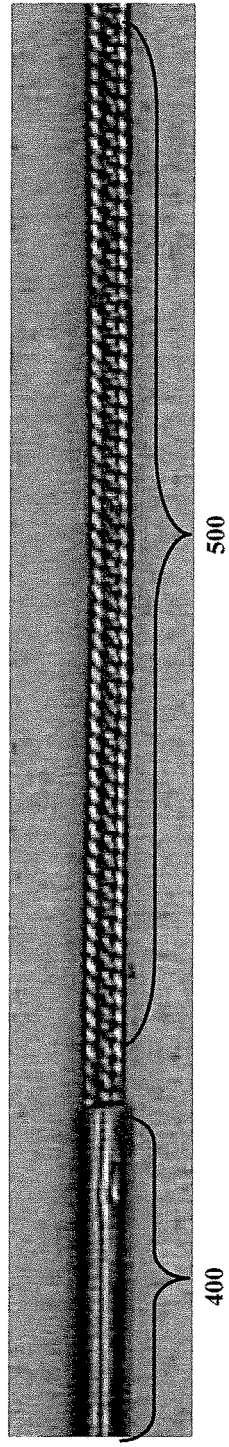
FIG. 9a is one embodiment of the rotary drive shaft.

Turning now to FIGS. 9-11, alternative embodiments of the rotary drive shaft 40 are illustrated. As discussed above, the rotary drive shaft 40 connects the distal end optical train and optics to the rotary motor and the transmission of rotary torque to the distal end optics while minimizing NURD. As shown in FIG. 9a, the rotary drive shaft 40 may comprise entirely of a hypotube metal drive shaft 400, a stranded hollow core shaft 500 or a combination of the hypotube metal drive shaft 400 joined with the stranded hollow core shaft 500, or alternating combinations of the hypotube metal drive shaft 400 and stranded hollow core shaft 500. The hypotube metal drive shaft may comprise nitinol, i.e. nickel titanium alloy, or another pseudometallic biocompatible alloy such as stainless steel, tantalum, gold, platinum, titanium, copper, nickel, vanadium, zinc metal alloys thereof, copper-zinc-aluminum alloy, and combinations thereof. Alternatively, the metal hypotube shaft 400 may include a reinforced telescoping inner assembly coaxially coupled over the proximal end of the metal hypotube shaft 400. The reinforced telescoping inner assembly is stronger than the metal hypotube shaft 400 to prevent buckling, bending, or shearing. The reinforced telescoping inner assembly includes a metal tube stainless steel design coupled to the centering boot to permit longer push-forward capability and provide improved liquid seal during flush.

Figure 9B:
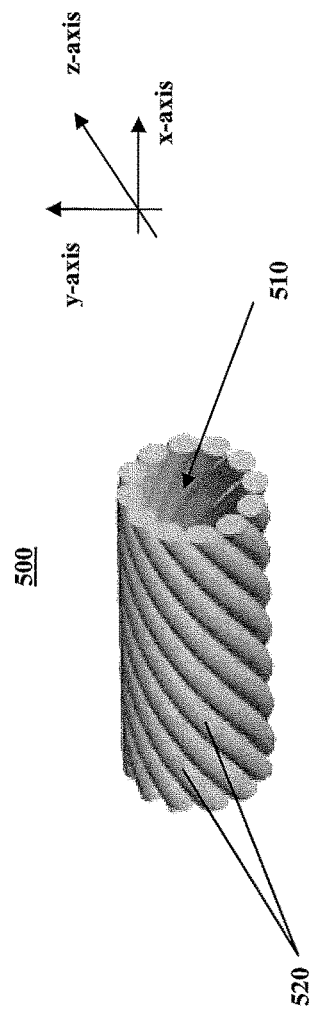
FIG. 9b is a perspective cross-sectional view of one embodiment of the rotary drive shaft.

As shown in FIG. 9b, the stranded hollow core shaft 500 comprises a stranded hollow core or lumen 510 including a plurality of helically wound metal wires 520. The helically wound metal wires 520 include an outer surface and a diameter, which may exist at about 0.002 to about 0.005 inches. The helical wound metal wires 520 are fixedly engaged with neighboring metal wires on their respective outer surfaces. The fixed engagement of the helical wound metal wires 520 completely encases the stranded hollow lumen 510. The stranded hollow core shaft 500 with the helical wound metal wires 520 are different from a spring coil wire, in that a spring coil wire consists of a single metal wire wound about itself in a helical fashion. The helically wound metal wires 520 may exist in any number to form the stranded hollow core shaft 500, in one embodiment from about 2 to 15 wires, from about 3 to 12 wires, or from about 4 to 10 wires in the helical configuration. An individual helical wound wire 520 may consist of only one metal filament; however, the individual helical wound wire 520 may include more than one metal filament. The helically wound metal wires 520 may comprise nitinol, i.e. nickel titanium alloy, or another pseudometallic biocompatible alloy such as stainless steel, tantalum, gold, platinum, titanium, copper, nickel, vanadium, zinc metal alloys thereof, copper-zinc-aluminum alloy, and combinations thereof. The stranded hollow core shaft 500 may be helically wound and that portion may consist of an inner helical stranded portion and an outer helical stranded portion. The inner helical stranded portion may wind in the opposite direction as the outer helical stranded portion. In one embodiment, the stranded hollow core shaft 500 may include a helical wound configuration including a Picks Per Inch (PPI), where there may be about 5 to 15, about 7 to 12 PPI, and about 8 to 10 PPP for the helical configuration. The helical wound configuration may have alternating symmetries along the longitudinal axis of the rotary drive shaft, such as an infinite helical symmetry, n-fold helical symmetry, and non-repeating helical symmetry. The stranded hollow core shaft 500 may be coated with some biocompatible material, such as PTFE or similar polymers to provide lubricity within the monolithic catheter sheath.

The distal part of the rotary drive shaft 40 may be the stranded hollow core 500 design, where flexibility is required at the entry point to the body. From the proximal portion to the distal portion of the rotary drive shaft 40, a single layer or double layer wound stranded hollow core may be included at the proximal portion, a hypotube metal drive shaft 400, and a single layer or double layer wound at the distal portion as to have a flexible distal tip.

The hypotube metal drive shaft 400 may include a solid wall extending substantially the entire longitudinal length of the central lumen of the rotary drive shaft 40 in combination with the stranded hollow core shaft 500, which (a) increases torsional rigidity of the rotating shaft and reduces NURD; (b) increases column strength or axial rigidity to improve the pushability of the catheter assembly; (c) reduces or eliminates the possibility of the stranded or coiled hollow core shaft unraveling or disassociating under the torsional forces applied; (d) improves the frictional interface by replacing an interrupted or more concentrated load transference between individual strands and the monolithic outer sheath with a continuous and more distributed load across the solid-walled hypotube metal shaft; and (e) the hypotube metal shaft offers a good fluid seal against the monolithic outer sheath over the proximal section of a fluid-filled catheter due to the solid-walled design.

Figure 10A:
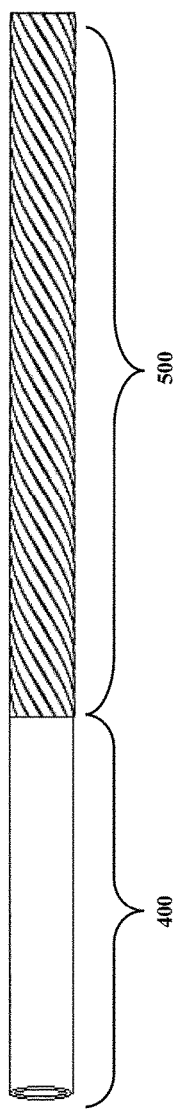
FIG. 10a is a side elevational view of an embodiment of the rotary shaft, and FIG. 10b a side elevational view of an embodiment of the stranded hollow core shaft.
Figure 10B:
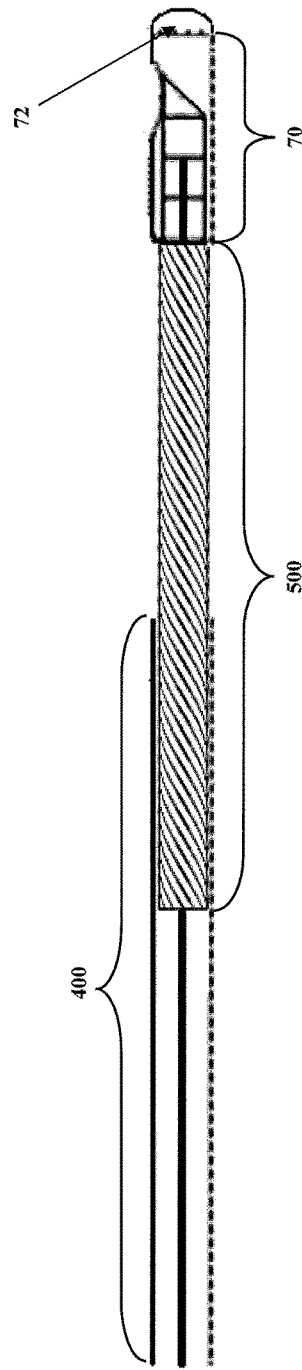

The solid-walled hypotube metal drive shaft 400 may, alternatively be used in conjunction with the stranded hollow core shaft by either butt-joining a distal end of the hypotube metal shaft 400 onto a proximal end of the stranded hollow core shaft 500, as illustrated in FIG. 10a. The butt-joining of the two ends may be accomplished by welding or adhesives to ensure little to no vibration during rotation. Alternatively, a portion of the hypotube metal shaft 400 may be concentrically or coaxially engaged or fitted with a portion of the stranded hollow core shaft 500, as is illustrated in FIG. 10b. The coaxial fitting ensures a 1:1 rotation of the hypotube metal shaft 400 and the stranded hollow core shaft 500 to ensure little to no vibration during rotation. The stranded hollow core shaft 500 is coaxially engaged with the protection bearing 70, where the protection bearing may include an epoxy rounded tip 72 to ensure smooth rotational translation of the protection bearing 70.

Longer sections of the hypotube metal shaft 400 may be employed proximal of the rotary drive shaft 40 to achieve a greater reduction of NURD. Due to its relative rigidity, the length of the hypotube metal shaft 400 should not extend too far distally so as to interfere with the distal flexibility of the catheter and prevent it from navigating tortuous anatomical passageways. The wall-thickness of the hypotube metal shaft 400 may be varied along its length to impart variable stiffness along the longitudinal axis of the hypotube metal shaft 400. In this manner, relatively thinner wall-thicknesses may be formed distally than those formed more proximally, to impart greater flexibility at the distal end of the hypotube metal shaft 400. The wall thickness may be varied by extrusion processing, mechanical means, such as grinding, abrasive blasting, turning, by chemical or electrochemical means, such as electro-polishing or etching, or by combinations of the foregoing. Alternatively, slots, holes or other aperture shape formations may be formed by means of cutting, etching, ablating or other means to generate designs in the tubular structure which permit additional flexibility of the distal region of the hypotube metal shaft 400 while retaining substantial torsional rigidity.

The rotary drive shaft 40 design can include the following considerations: (1) the material type and geometry of the material that comprise a given segment; and (2) a number of distinct material segments when progressing from the proximal to distal portions of the catheter.

In one embodiment, the design of the rotary drive shaft 40 includes setting the lateral flexibility of the material at the proximal end to a specific point and increasing the lateral flexibility from the proximal end to the distal segments of the rotary drive shaft. Generally speaking, a higher lateral flexibility is desired in portions of the catheter that experience the greatest geometric curvature when used for imaging. In addition, the diameter of the rotary drive shaft may become gradually or stepwise smaller from the proximal end to the distal portions of the rotary drive shaft. By reducing the wall thickness or by reducing the ID and OD or both the ID and OD, the diameter of the rotary drive shaft becomes smaller. The geometry of catheter at the surgical entry point and the geometry of the human coronary tract generally put these regions at the surgical entry point to the body and the aortic arch and the coronary blood vessel being interrogated.

The material type and the geometry of the materials in a given segment may vary in the rotary drive shaft. Different geometries are recognized for a given segment of the rotary drive shaft. Examples include, but are not limited to: (1) homogeneous solid (e.g., nitinol, PEEK, or some polymer); (2) stranded hollow core shaft (single wound, double counter-wound, or triple coil-wound or generally multiple wound); (3) braided multi-stranded hollow core shaft; (4) fibrous composite (fibers in a matrix); (5) patterned solid (#1 with patterned holes or apertures); and (6) patterned composite (#4 with patterned holes or apertures).

In one embodiment, the number of distinct segments may vary. A two segment rotary drive shaft includes the metal hypotube shaft in the proximal portion and a stranded hollow core at the distal portion. Other possibilities and combinations include, but are not limited to: (1) metal hypotube shaft proximal, and patterned metal hypotube shaft distal with a selected hole pattern, where the lateral flexibility of the solid metal hypotube shaft and patterned metal hypotube shaft may be graded when going from proximal to distal portions for increased flexibility; (2) a filament wound or fiber reinforced composite material at the proximal end with increased fiber density and a composite material at the distal end with a decreased fiber density (i.e., with increased lateral flexibility) or a fiber density that is graded downward going from the proximal end to the distal end; (3) a composite material at the proximal end with increased fiber density, nitinol in the mid-portion and stranded hollow core at the distal end. The joints between any segments may be joined end-to-end with for example a butt-couple, weld, epoxy or other jointing technique. Alternately, an overlapping style of joint may be used, i.e. male-female joints, or by coaxial engagement, concentric alignment, and the like. Connection of the segments of an overlapping style of joint may be accomplished by means of welding, adhesive, or over-molding given that at least one element is polymer.

In addition, a gradation, either gradual or stepwise, may be accomplished by a change in material properties along the length of the rotary drive shaft. For example, the material properties may be adjusted such as the modulus of elasticity of the material via methods including, but not limited to annealing, carburization, or heat treat and subsequent quenching techniques. In the case of nitinol, one may adjust the transition temperature ($A_f$) along the length by means of heat treatment, cold working, or some combination thereof. $M_f$ is the temperature at which the transition to Martensite is finished during cooling. Accordingly, during heating $A_s$ and $A_f$ are the temperatures at which the transformation from Martensite to Austenite starts and finishes. Nitinol is typically composed of approximately 50 to 55.6% nickel by weight. Making small changes in the composition can change the transition temperature of the alloy significantly. For this reason, nitinol may or may not be superelastic at certain temperatures, thus allowing the modulus of elasticity to be adjusted according to the temperature of use.

Characterizing Torsion, Bending, and NURD

Generally speaking, the angular deflection ($\theta$) for NURD in a homogenous hollow tube including a cross section is given by Equation (1):

$$\theta = TL/JG, \tag{1}$$

where $\theta$=Angular deflection, T=Torque, L=length of shaft, J=Polar Second Moment of Area, and G=modulus of rigidity (shear modulus). Since the Polar Second Moment of Area $J=\pi/32\ (d_o^4-d_i^4)$, then Equation (1) becomes:

$$\theta = \frac{TL}{\frac{\pi}{32}(d_o^4-d_i^4)G}. \tag{2}$$

The change in the angular velocity (i.e. the second derivative and angular deflection) is given by the following:

$$\frac{d^2\theta}{dt^2} = \frac{L}{JG} \cdot \frac{d^2T}{dt^2} \Rightarrow \frac{d^2\theta}{dt^2} = \frac{32L}{\pi G(d_o^4-d_i^4)} \cdot \frac{d^2T}{dt^2}, \tag{3}$$

where minimizing NURD is minimizing $$\frac{d^2\theta}{dt^2},$$

which can be achieved by minimizing L or T, and/or maximizing G or $\Delta d=d_o-d_i$. The load can be reduced by reducing the friction or by reducing the section modulus.

Figure 11A:
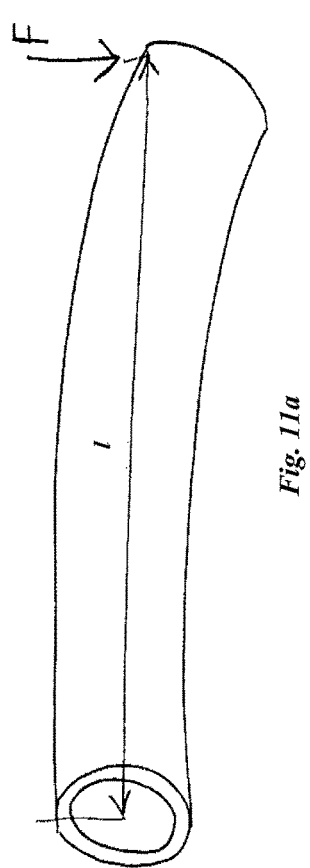
FIG. 11a is a perspective view of a tube undergoing a bending force F, FIG. 11b. is a cross-sectional view of the catheter traversing a bend in a bode vessel.

The bending load, as shown in FIG. 11a, is generally M=Fl, where M=the bending morphology, F is the Force (load on the tube), and l is the length. The Section modulus (S) is given by the equation S=I/C, and I is given by Equation (4):

$$I = \frac{\pi d^3 t}{8}, \tag{4}$$

where t is the thickness of the tube and d=2r, r is the radius of the tube. The load can be reduced by reducing the friction or by reducing section modulus S, which can rewritten as $$S = \frac{\pi d^3 t}{8C}.$$

The bending state $\sigma=M/S$ can be rewritten as:

$$\sigma = \frac{F \cdot l}{S} \Rightarrow \frac{S\sigma}{l} = F \tag{5}$$

The reduction of $S\sigma/l$ or the reduction of F will reduce the load. Alternatively, the load can be reduced by reducing the friction, which is dependent upon the material coefficient and force by equation (6):

$$F_k = \mu_k N, \tag{6}$$

where $F_k$ is the kinetic friction and $\mu_k$ is the coefficient of kinetic friction of material, and N is the normal force. The values of the coefficient of friction depend on many things, including, but not limited to the surface finish, coating, temperature, and the like. There are several contact points that are continuously changing during pullback which may consist of: (1) the surface of the stranded hollow core shaft strands (2) the ID of the FEP monolithic outer sheath if no water, fill solution, or coatings are present; and (3) the surface of the OD of the protection bearing to the ID of the FEP monolithic outer sheath if no water, fill solution, or coatings are present. Thus the normal force is between: (1) the shaft OD and sheath ID; and/or (2) the protection bearing OD and sheath ID.

Figure 11B:
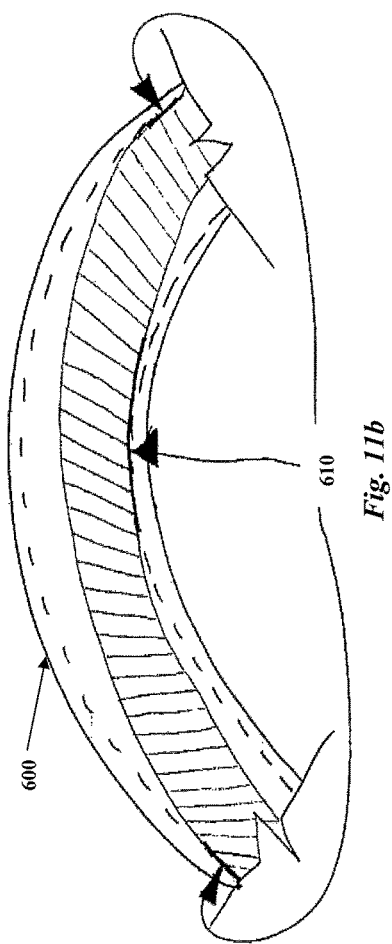
FIG. 11c is a cross-sectional view of the inner diameter (ID) and outer diameter (OD) of the hypotube.

As shown in FIG. 11b, the catheter, at any bending point in a vessel 600, there will be several friction points 610. Friction is a function of the normal force (N) between the drive shaft and the inner wall of the outer sheath, so then the bending moment is related to friction by the section modulus as follows: Friction force $F_k=\mu_k N$, Normal force $$N = \frac{S\sigma}{l}, \text{ and } S = \frac{\pi d^3 t}{8C} \text{ so}$$

then:

$$F_k = \frac{\mu_k S \sigma}{l}, \quad (7)$$

where $\mu_k$, $\sigma$, and $l$ are constants. By reducing the diameter (d) of the tube, a reduction of friction $F_k$ is achieved by the following equation:

$$F_k = \frac{\mu_k \sigma \pi d^3 t}{8cl}. \quad (8)$$

Reducing the diameter (d) reduces $$\frac{d^2\theta}{dt^2},$$

where $$\frac{d^2\theta}{dt^2} = \frac{L}{JG} \cdot \frac{d^2T}{dt^2}$$

and the reduction of Torque (T). Since G is material dependent (or structure dependent), a different material or structure may be used. J is dependent on $\Delta d$ by $J=\pi/32\,(d_o^4-d_i^4)$. Torque (T) $T=F\cdot l$, and the change in Force is represented by:

$$\Sigma F = F_{input} - F_k \quad (9)$$

By using Equation (8) and substituting $F_k$ for F results in:

$$T = \frac{\mu_k \sigma \pi d^3 t}{8c}, \quad (10)$$

where c is the distance to neutral axis, which is the case when d/2. By substituting d/2 for c gives the following:

$$T = \frac{\mu_k \sigma \pi d^2 t}{4}. \quad (11)$$

By substituting T and J into $$\frac{d^2\theta}{dt^2} = \frac{L}{JG}\frac{d^2T}{dt^2}$$

results in:

$$\frac{d^2\theta}{dt^2} = \frac{L}{\frac{\pi}{32}(d_o^4-d_i^4)G} \cdot \frac{d^2(\mu_k\sigma\pi d^2 t)}{dt^2(4)}.$$

The two competing mass moment of inertia terms are J and I. The two opposing factors are friction due to bending and torsional rigidity. Moment of inertial (I) from the section modulus in the bending portion is compared to the polar second moment of area (J).

Figure 11C:
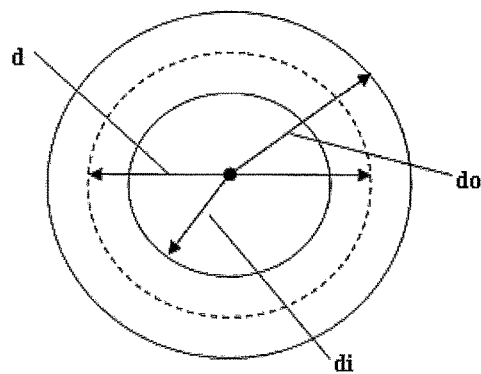

For a hollow circular cross section, $J=\pi/32\,(d_o^4-d_i^4)$, $$I = \frac{\pi d^3 t}{8},$$

where $c=d/2$, $d=(d_o+d_i)/2$ and $t=(d_o-d_i)/2$. As shown in FIG. 11c, $d_o$ is the outer diameter of the tube, $d_i$ is the inner diameter of the tube, and d is the diameter from the midsection of the tube. Substituting in terms of $(d_o+d_i)/2$ gives:

$$I = \frac{\pi(d_o+d_i/2)^3(d_o+d_i/2)}{8} \quad (12)$$
$$= \frac{\pi}{128}(d_o^4 - d_i^4 + 2d_o^3 d_i - 2d_o d_i^3),$$

and $$J = \frac{\pi}{32}(d_o^4 + d_i^4). \quad (13)$$

Figure 12A:
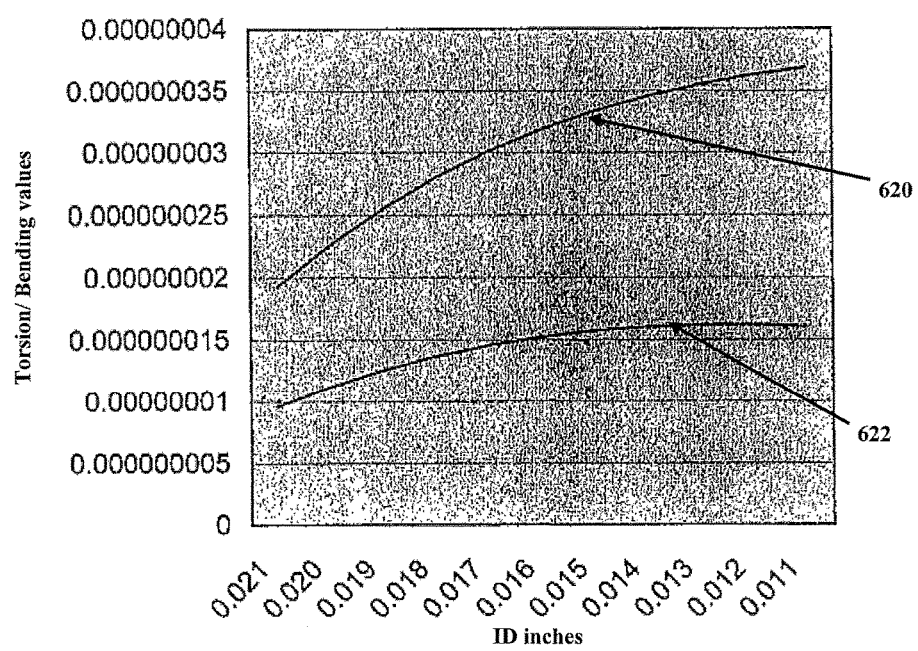
FIGS. 12a and 12b are graphs illustrating the torsion/bending ratio of one embodiment of the rotary drive shaft.
Figure 12B:
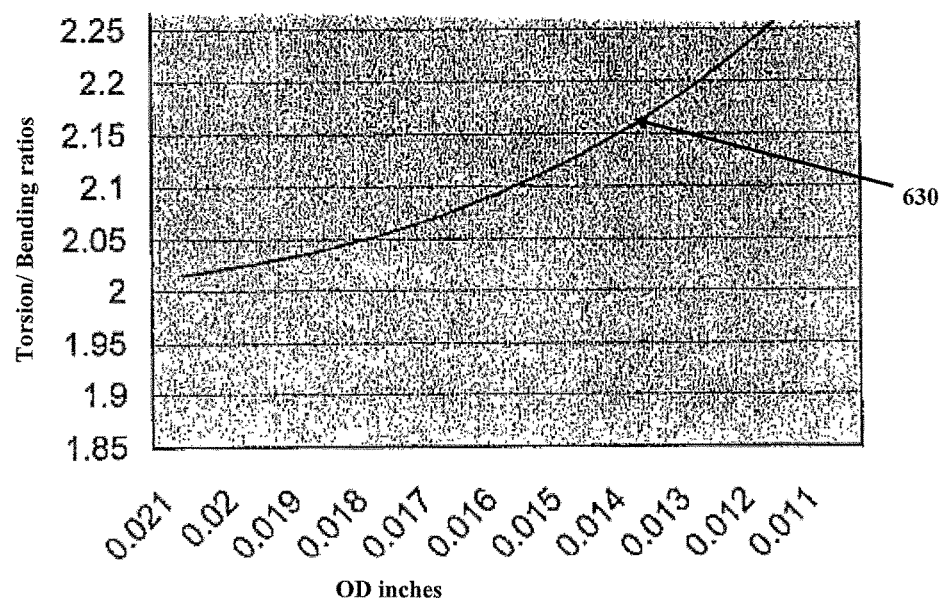

Comparing equation (12) and (13) by varying inner diameter (ID) from about 0.11-0.024 inches and the outer diameter (OD) from about 0.015-0.025 inches, and holding OD constant at 0.200 inches and 0.025 inches, produces the graphs as illustrated in FIGS. 12a and 12b.

FIG. 12a is a chart illustrating the Torsion Term 620 and the Bending Term 622. FIG. 12b is a chart illustrating the change in the Torsion/Bending Ratio 630 while measuring for NURD during angular deflection testing of the rotary drive shaft within an outer monolithic sheath. The characteristics of the rotary drive shaft and/or the outer monolithic sheath may be tested from various mechanical testing methods, such as tensile tests, torsion test, bending test or compression test. The torsion and bending tests provide useful information about the type of deformation of the rotary drive shaft and catheter monolithic sheath to account for NURD.

Active and Passive Characterizations of NURD

Figure 18:
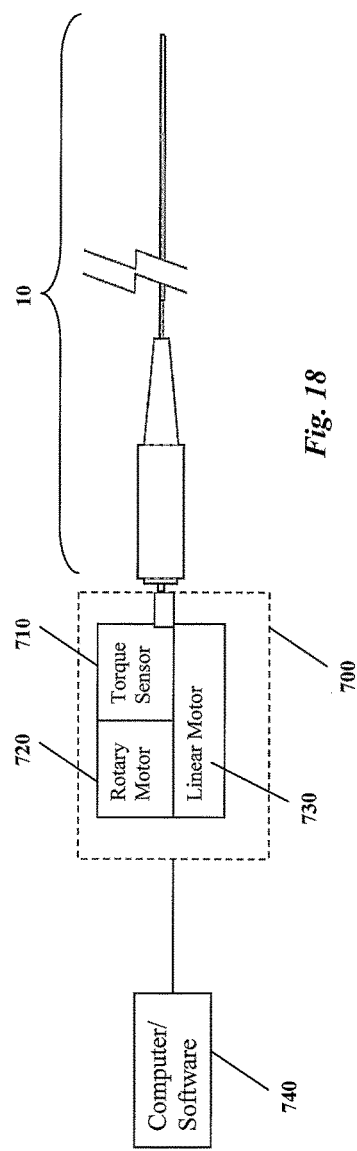
FIG. 18 is a schematic of the catheter 10 is coupled to the proximal motor system.

The measurement of rotary position of the catheter 10 may be used as input for a NURD-reduction software approach. As shown in FIG. 18, the catheter 10 is coupled to the proximal motor system 700, including a torque sensor 710, a rotary motor 720, a linear motor 730, and a computer/software program 740 operably coupled to the motor system 700. The method for estimating NURD in the rotational imaging catheter 10 is by measuring the torque on proximal end of the catheter 10 with the torque sensor 710. If NURD is characterized (e.g, in the form of an equation or data points representing angular position of imaging transducer vs. time) then removal of or correcting for NURD via post-processing of the image is straightforward. To truly characterize NURD, the angular position of the rotating imaging transducer must be known.

Methods for determining this position include active approaches such as distal accelerometers or passive approaches such as encoding a circumferential line pattern in the catheter outer sheath which can be detected within the image itself (OCT, IVUS, etc.) or encoding the catheter sheath thickness into the angular position and detecting within the OCT or IVUS image. An active method for estimating the angular position of the rotating imaging transducer as a function of time (i.e. rotational period) by measuring the slight variation in torque required to drive the catheter through one period of rotation ($2\pi$).

Figure 19:
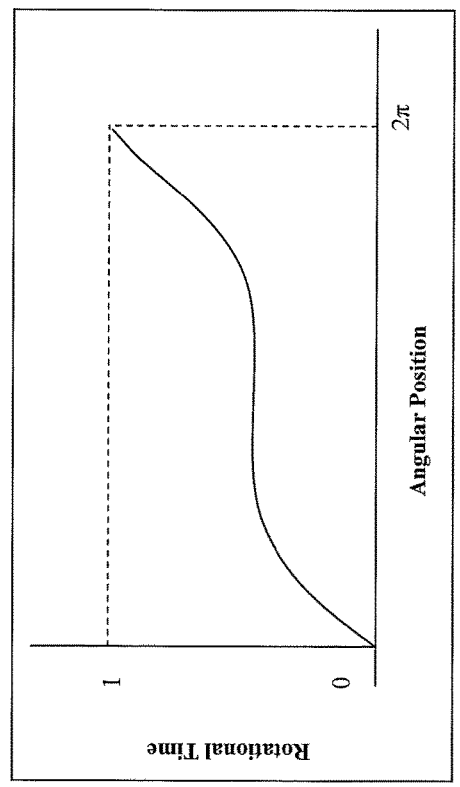
FIG. 19 is a graph of the angular position vs. rotational time.

The proximal torque measurement is indirect because measurements are made on the proximal end of the driveshaft, however the torsional properties of the driveshaft are known and constant, and thus the mechanical response of the distal tip can be estimated by the mechanical response of the proximal shaft. Knowledge of the angular position vs. time is shown in FIG. 19, and is an important input to correct for NURD. The y-axis of the graph in FIG. 19 is the rotational time, where 1 rotation has occurred.

A passive method for indirectly determining the angular position of the rotating imaging transducer 750 as a function of time (i.e. rotational period) is by forcing the rotating transducer to be in an eccentric location with respect to the outer wall of the stationary sheath.

As shown in FIG. 20a, the outer wall of the stationary sheath 752 can be visualized in the image and because it is eccentric with respect to the transducer rotation. The outer sheath 752 includes a thickness S. The outer wall of the stationary sheath will experience a geometrical image distortion (i.e. the apple-like cross-sectional shape) when NURD is present and the catheter is not centered on the vessel axis, as shown in FIG. 20b. The eccentricity of the rotating portion with respect to the outer sheath 752 must only be large enough to visualize in the image (i.e. the difference in wall thickness as a function of angle due to the eccentricity must be larger than the depth resolution of the imaging modality).

To create a representation of angular position vs. rotational period, the image of the outer sheath 752 outer diameter OD 754 and the wall thickness S is compared to the a priori known eccentricity of the sheath. This comparison can be based on curve fitting to analytical models, statistical decision tree, or other numerical methods. The method for determining the thickness data from the angular position of a sensor within a catheter having a sheath wall of varying thickness can be found in U.S. Pat. No. 6,450,964, incorporated by reference herein.

The beam distortion (e.g. astigmatism) from the eccentrically oriented sheath will be minimal because the wall thickness vs. angle can be small relative to the beam diameter as it passes through the sheath. This can be further minimized by matching the wave speed in the sheath material with the fluid media bordering the ID and OD of the sheath (i.e. refractive index if OCT, acoustic impedance if ultrasound).

Examples

The following examples are put forth so as to provide those of ordinary skill in the art with a complete disclosure and description of how the articles, devices, systems, and/or methods claimed herein are made and evaluated, and are intended to be purely exemplary and are not intended to limit the scope of articles, systems, and/or methods. Efforts have been made to ensure accuracy with respect to numbers (e.g., amounts, temperature, etc.), but some errors and deviations should be accounted for.

Figure 13:
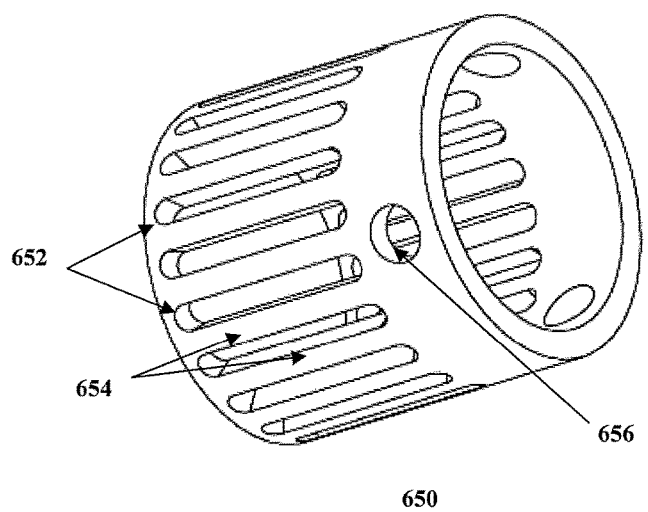
FIG. 13 is perspective schematic view of the NURD mask for the catheter system.

OCT images of a NURD mask for the catheter with a vessel in phantom are shown in FIGS. 14, 15, and 16. The examples span the range from mild to moderate NURD with for each case the angular position vs. time and the resulting B-scan profile. The catheter OCT system records 1000 A-lines per rotation. A tube called a resolution mask or NURD mask 650 is placed over the catheter system, as shown in FIG. 13. The NURD mask 650 may include several different sizes to measure the effects of NURD at different diameters. The NURD mask includes a plurality of slots 652, where the widths of the slots may range from about 0.157 to about 0.314 mm. The slots 652 intervene with struts 654. The slot width and strut width may be equal in diameter to give 20 slots 652 around the circumference of the NURD mask 650. No slag or burrs shall be present on finished NURD mask 650. The NURD mask 650 may include an aperture 656 to secure the NURD mask 650 to the catheter. The diameter of the aperture 656 may range from 0.3-0.6 mm. The NURD mask 650 may be constructed from metal, stainless steel, nitinol, and the like.

Figure 14A:
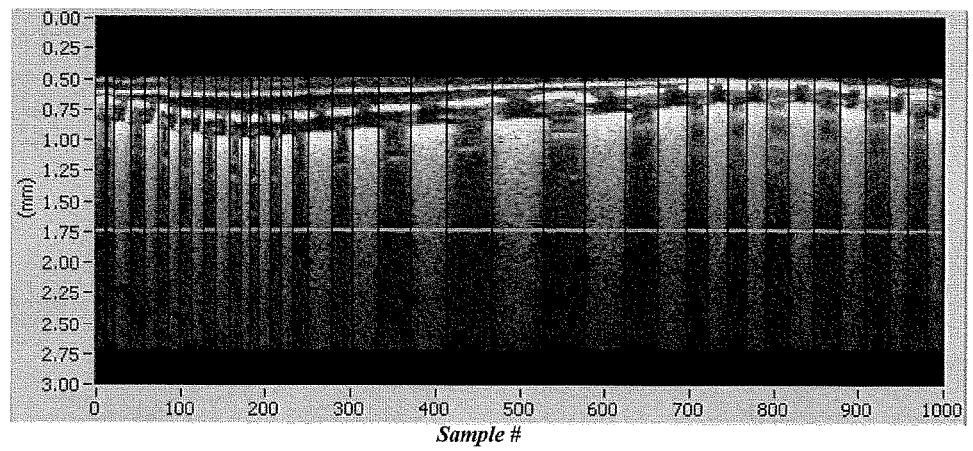
FIG. 14a is a recorded rectangular OCT images of a NURD mask for the catheter with moderate NURD.
Figure 14B:
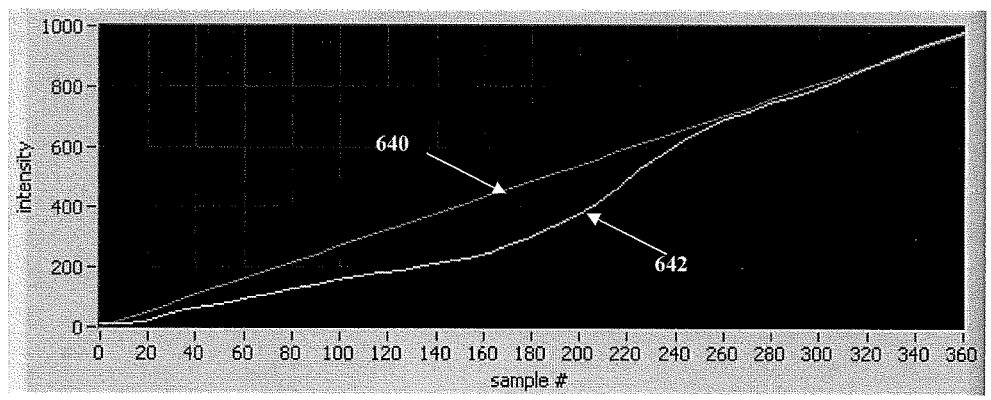
FIG. 14b is a graph of the angular position of the imaging beam versus time for one rotation, the X-axis (sample #) equals degrees in a single rotation of catheter inner member, and the Y-axis is the A-scan number where one full rotation corresponds to 1000 A-scans.

As shown in FIG. 14a, a rectangular OCT image of the NURD mask 650 with moderate NURD, where the NURD mask 650 includes 20 evenly spaced slots and where the tube slot width equals the tube strut width. The x-axis is sample number on the graph of FIG. 14a and the vessel is in phantom. As shown in FIG. 14b, a chart showing where the actual imaging beam is at any given point in time for one rotation, X-axis (sample #)=degrees in a single rotation of catheter inner member, Y-axis (intensity)=period of rotation divided into 1000 discrete points. The theoretical line for no NURD 640 is the non-white curve, the actual measured NURD 642 is the white curve, and the vertical distance between the white actual measured NURD 642 and non-white theoretical line 640 for no NURD determines the amount of NURD. For example, the more distance between the non-white theoretical line 640 for no NURD and the white actual measured NURD 642 indicates more NURD. For FIG. 14b, moderate NURD is shown between samples #160 and #200.

Figure 15A:
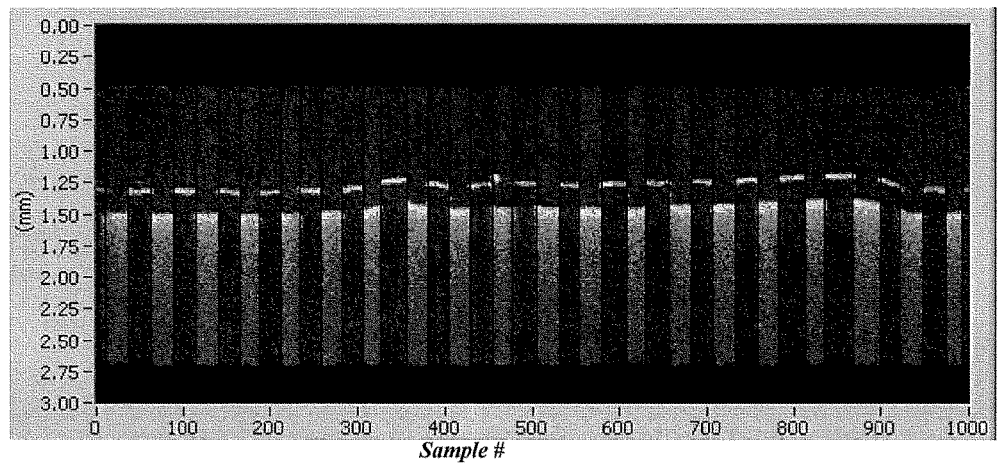
FIG. 15a is a recorded rectangular OCT image of a NURD mask for a catheter with minimal NURD, and 15b is a graph of the angular position of the imaging beam versus time for one rotation, the X-axis (sample #) equals degrees in a single rotation of catheter inner member, and the Y-axis is the A-scan number where one full rotation corresponds to 1000 A-scans.
Figure 15B:
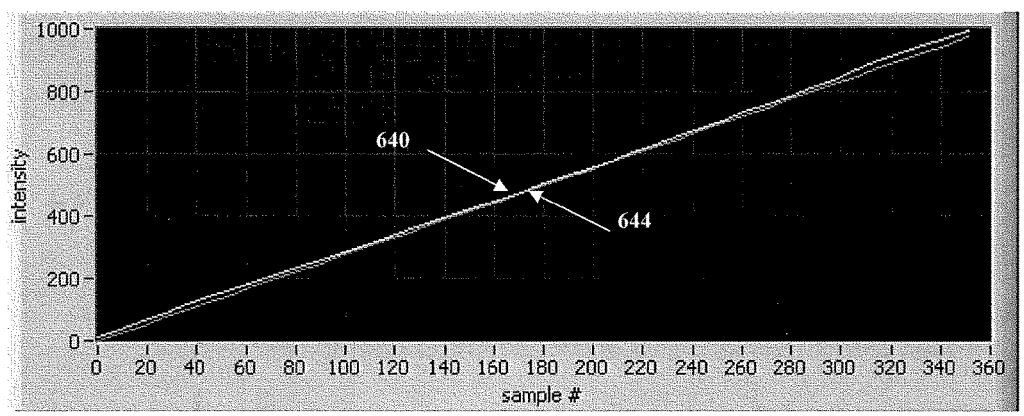

As shown in FIG. 15a, a rectangular OCT image of the NURD mask with minimal NURD with the image of the NURD mask including 20 evenly spaced slots, and where the tube slot width equals the tube strut width. The x-axis is sample number on the graph of FIG. 15a and the vessel is in phantom. As shown in FIG. 15b, the chart shows where the actual imaging beam is at any given point in time for one rotation X-axis (sample #)=degrees in a single rotation of catheter inner member. Y-axis=A-scan number with 1000 A-scans per rotation. The theoretical line for no NURD 640 is the non-white curve, the actual measured NURD 644 is the white curve, and the vertical distance between the white actual measured NURD 644 and the non-white theoretical line 640 determines the amount of NURD. For example, the more distance between the non-white theoretical line 640 for no NURD and the white actual measured NURD 644 indicates more NURD. For FIG. 15b, minimal NURD is shown between samples #1 and #360, with little to no vertical distance between the non-white theoretical line 640 and the white actual measured NURD 644.

Figure 16A:
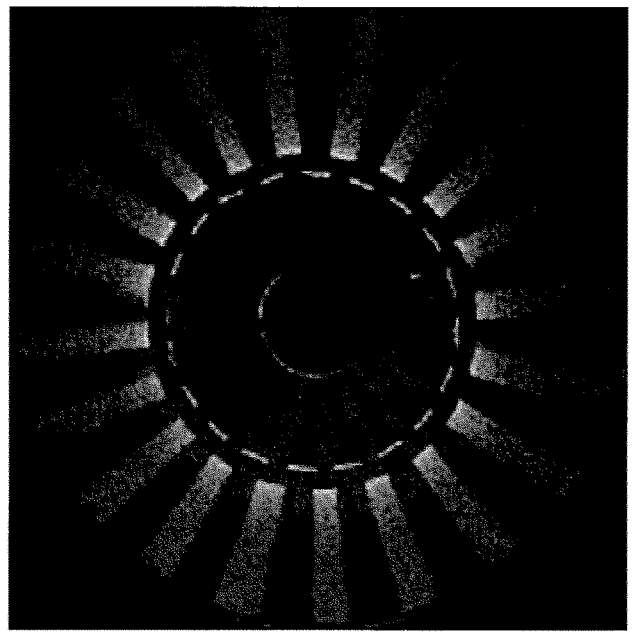
FIGS. 16a-16c are polar OCT images of a NURD mask.
Figure 16B:
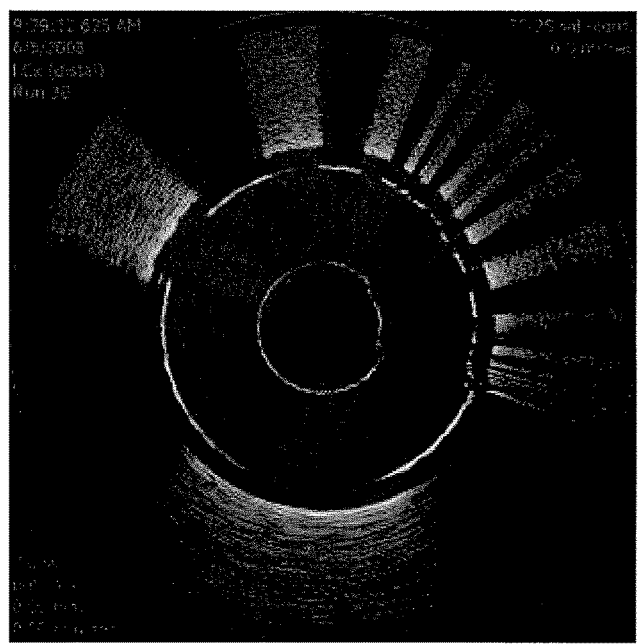
Figure 16C:
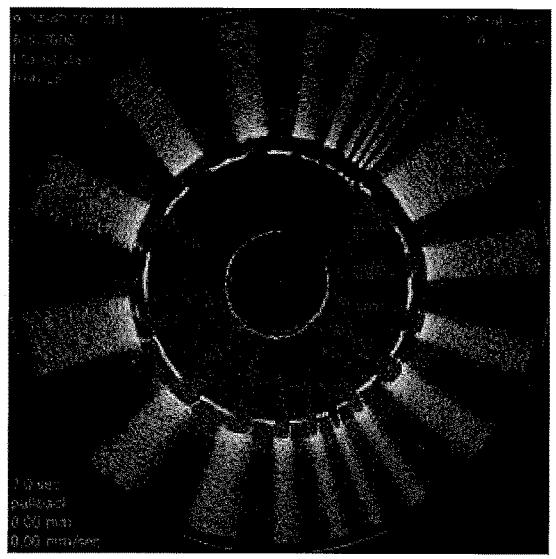

FIGS. 16a-16c show polar images of the OCT catheter 10 system with the NURD mask. FIG. 16a shows the catheter 10 in a straight vessel where the NURD is small. FIG. 16b shows the catheter with the NURD mask in a sharp 90 bend in the distal end where the NURD is small. FIG. 16c shows the catheter in a tortuous model LAD Co-Pilot within a tight valve and small NURD values. The polar images in FIGS. 16a-16c show the OCT catheter 10 in the center of the vessel. The lack of radial distortion may be due to the centering of the OCT catheter. The catheter is centered in the images of the NURD mask in the vessel phantoms and the apple shape of the radial distortion only appears when the catheter is offset from the center.

Figure 17A:
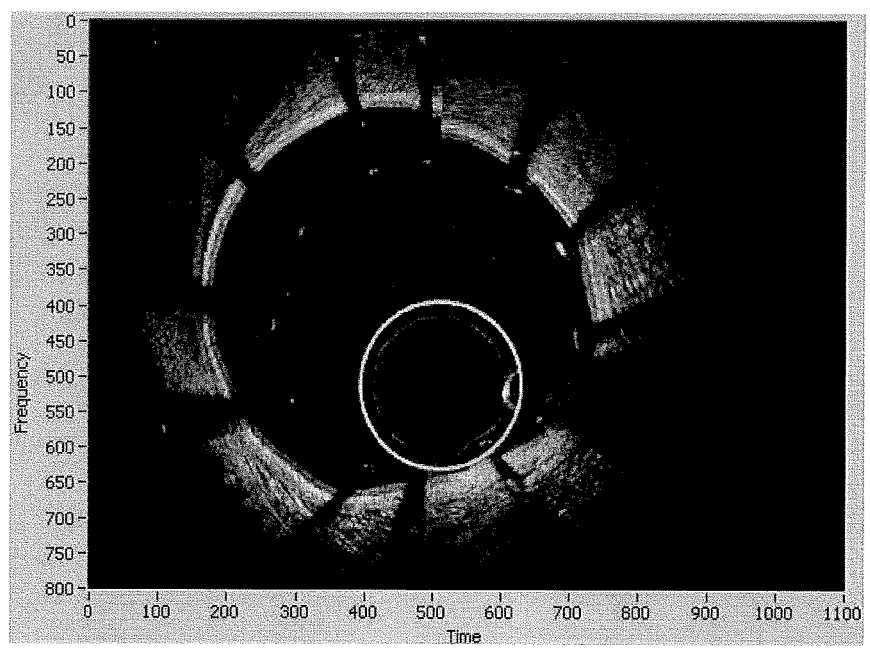
FIGS. 17a-17c are in vivo polar images recorded in a pig coronary artery placed with a stent demonstrating the simulated NURD effects in the same image.
Figure 17B:
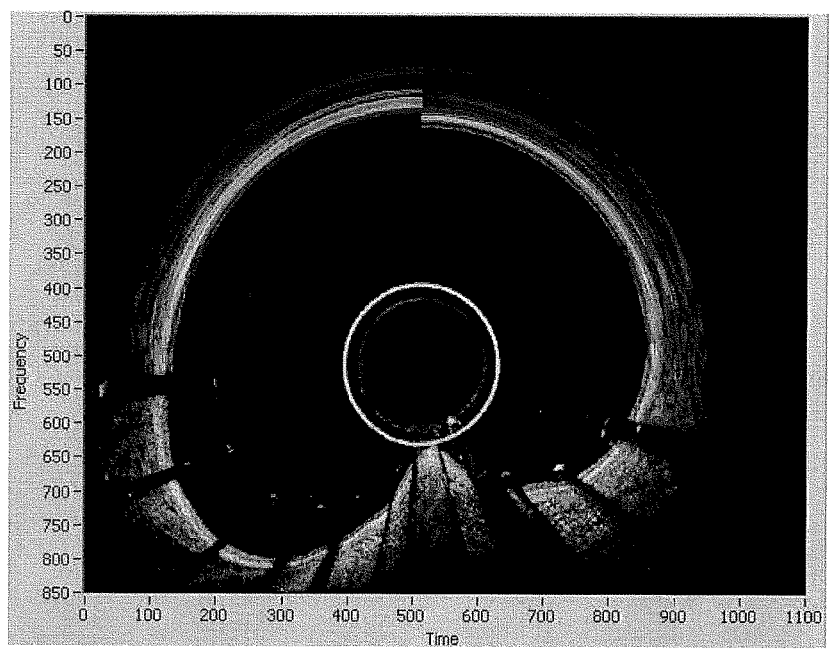
Figure 17C:
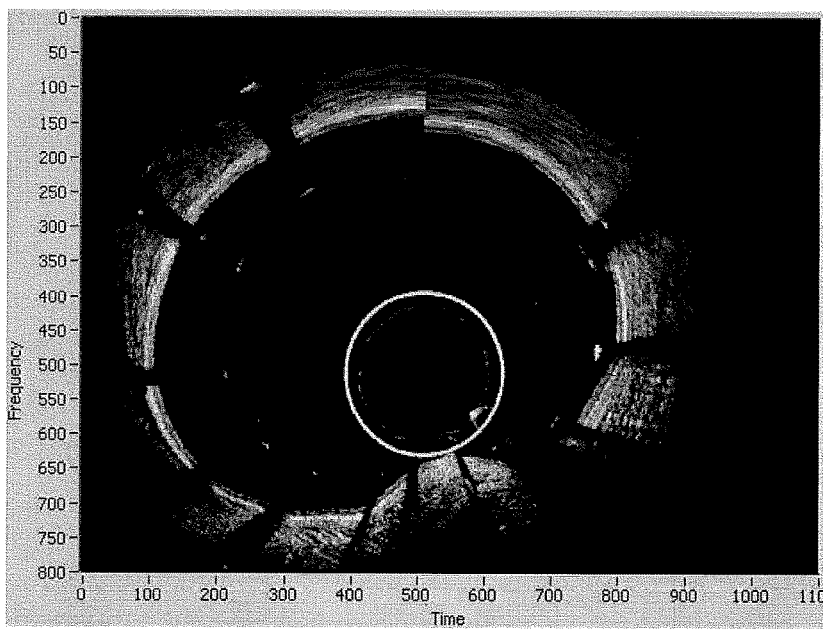

FIGS. 17a-17c are polar OCT images demonstrating the simulated NURD effects in the same image where the catheter is not centered can show an apple-like shape of the vessel. The image was recorded with the catheter 10 in vivo in a pig coronary placed with a stent. In order to see the apple-like cross sections of the radial distortion, the catheter can be positioned in an off-center position. FIG. 17a is an image showing original/less NURD. In the original/least NURD case, the catheter is off center in the vessel lumen and the slots are fairly evenly spaced radially around the perimeter. A simulation NURD program was created to simulate NURD with the catheter, vessel, etc. in the FIG. 17a image in post-processing steps. FIG. 17b is a simulated image showing medium NURD. As the NURD increases compared to the original image (FIG. 17a), the lumen cross section is increasingly warped with the characteristic apple shape and the stent strut spacing becomes more irregular. FIG. 17c is a simulated image showing extreme NURD, with the lumen warped into an apple-like shape. FIGS. 17a-17c suggest that a non-centrally located catheter in combination non-uniform rotational velocity can result in azimuthal and radial distortion in the polar OCT image.

Additional objects, advantages and novel features of the embodiments as set forth in the description, will be apparent to one skilled in the art after reading the foregoing detailed description or may be learned by practice of the embodiments. The objects and advantages of the embodiments may be realized and attained by means of the instruments and combinations particularly pointed out here.

What is claimed is:

1. A catheter for in vivo imaging comprising:
   a catheter sheath body defining a central lumen and a distal tip, the central lumen terminating at the distal tip and the distal tip having a guidewire lumen formed therein, the guidewire lumen being separate from the central lumen and having a guidewire entrance port and a guidewire exit port, the guidewire entrance port and the guidewire exit port each being positioned distal to the termination of the central lumen; and
   an optical train positioned within the central lumen, the optical train comprising a rotary drive shaft configured to rotate a distal end imaging assembly about a longitudinal axis, the rotary drive shaft comprising a proximal hypotube shaft having a distal end overlapping a proximal end of a distal single-layer stranded hollow core shaft, wherein the stranded hollow core shaft comprises helically wound metal wires fixedly engaged with neighboring metal wires on their respective outer surfaces.

2. The catheter of claim 1, wherein the catheter sheath body is a monolithic sheath body that includes a single continuous piece of material containing no joints from the proximal end of the sheath body to the distal end of the distal tip.

3. The catheter of claim 1, wherein the imaging assembly comprises an optical fiber, a gradient index lens, a prism, a housing concentrically engaged about the optical fiber, the gradient index lens, and the prism, and wherein the rotary drive shaft is coupled to a proximal end of the housing.

4. The catheter of claim 3, wherein the housing further comprises a metal tube having an opening in a wall thereof, the opening being in optical alignment with the prism.

5. The catheter of claim 3, wherein the rotary drive shaft defines a rotary drive shaft lumen and the distal stranded hollow core shaft of the rotary drive shaft is coupled to the housing, wherein the optical fiber passes axially through the rotary drive shaft lumen.

6. The catheter of claim 5, wherein the stranded hollow core shaft comprises a plurality of wires wound in a helical configuration.

7. The catheter of claim 1, further comprising a second housing coupled to the proximal hypotube of the rotary drive shaft.

8. The catheter of claim 1, wherein the monolithic sheath body further comprises a sheath material which is at least partially optically transparent.

9. The catheter of claim 1, wherein the guidewire entrance port opens to a distal end of the distal tip and the guidewire exit port opens to a side wall of the distal tip.

10. The catheter of claim 1, wherein a distal portion of the sheath body has a greater flexibility that a proximal portion of the sheath body.

11. The catheter of claim 1, wherein the durometer of the sheath is varied along the length of the monolithic catheter sheath to reduce non-uniform rotational distortion.

12. The catheter of claim 1, wherein the guidewire lumen includes a diameter that is varied from the proximal portion to the distal tip.

* * * * *